US006194200B1

(12) United States Patent
Rose et al.

(10) Patent No.: US 6,194,200 B1
(45) Date of Patent: Feb. 27, 2001

(54) EXPRESSION SYSTEMS FOR PREPARATION OF POLYPEPTIDES IN PROKARYOTIC CELLS

(75) Inventors: Timothy M. Rose; A. Gregory Bruce, both of Seattle, WA (US)

(73) Assignee: Oncogen, Seattle, WA (US)

(*) Notice: Subject to any disclaimer, the term of this patent is extended or adjusted under 35 U.S.C. 154(b) by 0 days.

(21) Appl. No.: 07/993,482

(22) Filed: Dec. 18, 1992

Related U.S. Application Data

(60) Continuation of application No. 07/750,710, filed on Aug. 20, 1991, now abandoned, which is a division of application No. 07/264,098, filed on Oct. 28, 1988, now abandoned, which is a continuation-in-part of application No. 07/240,768, filed on Sep. 2, 1988, now abandoned, which is a continuation-in-part of application No. 07/115,139, filed on Oct. 30, 1987, now abandoned.

(51) Int. Cl.[7] ............................ C12N 15/71; C12N 15/72

(52) U.S. Cl. ...................... 435/320.1; 536/24.1; 435/69.1

(58) Field of Search ............................... 435/69.1, 172.1, 435/172.3, 320.1, 252.33; 536/23.4, 24.1; 935/6, 22, 24, 33, 38, 39, 41, 43, 44, 45, 46, 47, 48

(56) References Cited

U.S. PATENT DOCUMENTS

| | | | |
|---|---|---|---|
| 4,543,329 | 9/1985 | Daum et al. | 435/69.1 |
| 4,565,785 | 1/1986 | Gilbert et al. | 435/69.1 |
| 4,582,800 * | 4/1986 | Crowl | 435/69.1 |
| 4,711,845 | 12/1987 | Gelfand et al. | 435/69.1 |

FOREIGN PATENT DOCUMENTS 196864 10/1986 (EP).

OTHER PUBLICATIONS

Engler et al., Sep. 5, 1988, J. Biol. Chem. 263:12384–12390.

Miyake et al., 1985, Chem. Abstra. 103(3):153–154.

Oka et al., 1985, Proc. Natl. Acad. Sci. USA 82:7212–7216 ("Oka I").

Oka et al., 1987, Agric. Biol. Chem. 51(4):1099–1104 ("Oka II").

Tachibana et al., 1987, J. Gen. Microbiol. 133:1775–1782.

F. Marcus, Chemical Abstracts "Preferential cleavage of aspartyl–prolyl peptide bonds in dilute acid" (Aug. 19, 1985) vol. 103, No. 7, p. 616, col. 2.

M. Zabeau, et al., *The EMBO Journal* "Enhanced expression of cro–beta–galactosidase fusion proteins under the control of the $P_R$ promoter of bacteriophage lambda" (Dec. 1982) vol. 1, pp. 1217–1224.

T. Miyake, et al., Chemical Agstracts "Secretion of human interferon–alpha induced by secretion vectors containing a promoter and signal sequence of alkaline phosphatase gene of *Escherichia coli*" (Jul. 22, 1985) vol. 103, No. 3, p. 153, col. 2.

D.H. Gelfand, et al., Chemical Abstracts "Monitoring and control systems for recombinant manipulations" (Feb. 17, 1986) vol. 104, No. 7, p. 149.

S. Chang, et al., Chemical Abstracts "Alkaline phosphatase mediated processing and secretion of recombinant proteins, DNA sequences for use therein and cells transformed using such sequences" (Apr. 27, 1987) vol. 106, No. 17, p. 149.

Mohammed et al. 1988. Amphoguline Antifunctional growth modulated clycoprotein . . . Proc Natl. Res. Sci USA 85:6528.*

Niyake et al. 1985. Secretion of human Inf–x indeed by using secretion rectors containing a promoles & signal sequence of phoa of *E Coli* J. Biochem 97:1429. Chemical Ab. 103:#17753r.*

T. Chang et al. 1985 pho–A mediated processing & secretion of iccombia proteins. Eur. Pat. Appl. EP 196,864. Chem. Ab 103:133062a.*

Gorski et al. Stability of Backesiophage T4 Gene 32 in RNA Cell 43:461 (1985).*

Namiahs et al. 1982 Moleculer Cloning. CSH pp. 226–227 and 408–433 and 507–520.*

Narcens 1985. Preferential cleavage of aspartyl–prolyl peptide bonds in dilute acid. Int. J. Pept. Protein Res. 25(5):542. Chemical Abs. vol. 103 #5444.*

Zabeam et al. 1982. Enhanced expression of cro–b–galactosidase fusion proteins under control of the $P_R$ promoters of λ. EMBO J. 1:1217.*

* cited by examiner

*Primary Examiner*—David Guzo
(74) *Attorney, Agent, or Firm*—Pennie & Edmonds LLP

(57) ABSTRACT

Expression cassettes for enhanced expression and production of a polypeptide of interest in prokaryotic cells are provided. The expression cassettes provide for production of the polypeptide of interest so that such polypeptide can either be secreted from the host cell in an active conformation or conveniently processed and renatured to a functional state. Preferably, the polypeptide of interest is expressed as a fusion protein, particularly fused to a leader sequence from a highly expressed bacterial or bacteriophage gene. The polypeptide of interest may subsequently be cleaved from the leader sequence and refolded, or used as a fusion protein.

1 Claim, No Drawings

EXPRESSION SYSTEMS FOR PREPARATION OF POLYPEPTIDES IN PROKARYOTIC CELLS

CROSS-REFERENCE TO RELATED APPLICATION

This a continuation of application Ser. No. 07/750,710, filed Aug. 20, 1991, now abandoned, which is a division, of application Ser. No. 07/264,098, filed Oct. 28, 1988, abandoned, which is a continuation-in-part of U.S. application Serial No. 240,768, filed Sep. 2, 1988, abandoned which is a continuation-in-part of U.S. application Ser. No. 115, 139, filed Oct. 30, 1987, abandoned, which disclosures are hereby incorporated herein by reference.

INTRODUCTION

1. Technical Field

This invention relates to compositions and methods for preparation of novel polypeptides, in particular fusion polypeptides, using recombinant DNA techniques.

2. Background

The advent of genetic engineering brought with it the promise of easy production of large quantities of a variety of peptides. However, this promise has not been fully realized for a number of reasons. For example, in many instances where the peptide has been produced and retained in the cytoplasm of the host organism, inclusion bodies have resulted requiring denaturation and renaturation of the protein, frequently with only partial or little success. In other instances, the peptide has been substantially degraded so that not only are yields low, but also complicated mixtures are obtained, which are difficult to separate.

As a potential solution to these difficulties, the possibility of obtaining secretion of a desired peptide into the nutrient medium has been investigated. Obtaining secretion of the desired protein has met with limited success in the past, since not all proteins are capable of being secreted by the host cells which have been employed. Moreover, even when secreted, the processing of the peptide by the host cell may result in a product which differs from the composition and/or conformation of the desired polypeptide and the yields of protein have been less than expected. There is, therefore, a substantial interest in developing systems for the efficient and economic production of active peptides where the desired polypeptide can accumulate in the host cell without degradation and can either be secreted in an active conformation or conveniently processed and renatured to a functional state.

SUMMARY OF THE INVENTION

Expression cassettes, and methods for their preparation and use are described, which provide for enhanced expression and production of an active gene product. The expression cassettes include efficient transcriptional and translational initiation and termination regulatory regions appropriate for the host cell to provide for expression of a desired polypeptide. The expression cassette preferably further includes, as appropriate for the host cell, a leader sequence for expression under the transcriptional and translational regulation of the regulatory region, sequences providing for enzymatic or chemical cleavage sites for cleavage of the leader peptide from mature polypeptide, and regulatory sequences which allow the time of expression of the gene of interest to be modulated. The expression cassettes are introduced into a host cell under conditions whereby the resulting transformants stably maintain the expression cassette. Naturally occuring DNA and synthetic genes may be employed for the production of a polypetide of interest.

DESCRIPTION OF THE SPECIFIC EMBODIMENTS

In accordance with the subject invention, expression cassettes are provided which, when inserted into a host cell, allow for the preparation of a polypeptide of interest which has enhanced stability and is either secreted in an active conformation or may be conveniently processed and renatured to an active state.

To obtain increased expression of a polypeptide of interest in a host cell, the nucleotides encoding the N-terminal amino acids of the polypeptide of interest are modified within the constraints of codon degeneracy to mimic those of the natural gene sequence found with the Shine-Dalgarno sequence used in the expression cassette. The expression cassette thus will have the following general structure:

$$P\text{--}S.D.\text{--}met\text{--}G_1$$

wherein

P comprises a promoter sequence including the regulatory regions occurring at about −35 and −10 nucleotides upstream from the start of the RNA chain and may also include regulatory sequences allowing for the induction of regulation;

S.D. comprises a Shine-Dalgarno sequence;

met comprises a codon for the initiating methionine of the polypeptide of interest; and $G_1$ comprises the gene for the polypeptide of interest wherein the first 7 to 30 codons of the gene have been modified wherever possible, using codon degeneracy to approximate the nucleotide sequence of the natural gene which would follow the Shine-Dalgarno sequence used in the expression cassette.

As an alternate means of obtaining increased expression of the polypeptide of interest from the host cell, the polypeptide can be expressed as a fusion protein by including in the expression cassette a DNA sequence encoding a leader sequence peptide joined in reading frame upstream from the gene of interest. Expressing the polypeptide of interest as a fusion protein can result in up to 30% or more of the protein produced by the host cell being the polypeptide of interest. The expression cassette for expressing a fusion protein will thus have the following basic structure:

$$P\text{--}S.D.\text{--}met\text{--}L\text{--}G$$

wherein:

P, S.D. and met have the meaning described above;

G comprises a gene for the polypeptide of interest; and

L comprises a DNA sequence encoding a leader peptide which may be an N-terminal sequence from any bacterial or bacteriophage gene, but generally is from a highly expressed gene; an amino acid sequence containing large numbers of hydrophobic amino acid residues; or an amino acid sequence containing large numbers of hydrophilic amino acid residues. When L comprises a hydrophobic amino acid sequence, this sequence will preferably also function as a signal sequence, allowing secretion of the polypeptide of interest from the host cell and cleavage of the signal sequence from the polypeptide. The DNA sequence coding for L may also be modified wherever possible, using codon degeneracy to approximate the nucleotide sequence of the natural gene which would follow the Shine-Dalgarno sequence used in the expression cassette.

The expression cassette described above provides for a fused expression product comprising the leader peptide and the polypeptide of interest. If it is desired to obtain the polypeptide of interest alone and there is no convenient cleavage site, e.g. as provided by a natural signal sequence, a cleavage site may be provided for by joining at least one codon encoding a cleavage site in reading frame upstream from the gene of interest. The cassette will thus have the following structure:

P--S.D.--met--L--C--G wherein P, S.D., met, L and G have the meaning described above and C comprises at least one codon providing for a chemical or enzymatic cleavage site.

To stabilize the mRNA and to provide for higher levels of expression of a desired polypeptide, a transcriptional termination region (T) can be included in the expression cassette downstream from the gene of interest. An example of an expression cassette comprising T is as follows:

P--S.D.--met--G--T although T may be included in any of the expression cassettes as described above.

Construction of Expression Cassettes

Design of an expression system to yield high levels of gene product must take into consideration not only the particular regions of a gene which have been determined to influence expression but also how these regions (and thus their sequences) influence each other. Where possible, choice of appropriate regulatory sequences will take into account the various factors which affect expression. Different genes have evolved a combination of all of these factors to yield a particular rate of expression; thus highly expressed genes can be considered useful models.

In terms of transcriptional regulation, the amount and stability of messenger RNA are important factors which influence the expression of gene products. The amount of mRNA is determined by the copy number of a particular gene, the relative efficiency of its promoter and the factors which regulate the promoter, such as enhancers or repressors. Initiation is believed to occur in the region just upstream of the beginning of the coding sequence.

The promoter in prokaryotic cells comprises nucleotide sequences which can affect the efficiency of transcription. These sequences include the regulatory regions at about −35 and −10 nucleotides from the start of the RNA chain. Efficient promoters include those in which the nucelotide sequence of the −35 and −10 regulatory regions is substantially the same as consensus sequences for these regions in bacterial promoters from highly efficient genes. Generally these regions are about 5 nucleotides and 6 nucleotides, respectively, in length, and each sequence may vary by about 1 nucleotide in length and/or in sequence. A preferred sequence for the −35 consensus regulatory sequence is from the trp promoter, namely TGACA, and for the −10 consensus regulatory sequence is from the lac promoter, namely TATAAT.

Not only the nucleoide sequences but also the spacing of the consensus sequences of the −35 and −10 regulatory regions, with respect to each other, is important for obtaining optimum transcription of the gene of interest. Generally, the consensus sequences of the −35 and −10 regulatory regions are separated by about 16 to 18 nucleotides, preferably by about 17 nucleotides.

Illustrative transcriptional regulatory regions or promoters which provide for efficient transcription include the β-gal promoter, lambda left and right promoters, the trp and lac promoters and trp-lac (tac) fusion promoters, and the like. Synthetic promoters having sequences substantially similar to these sequences may also find use. A preferred promoter is a fusion promoter comprising the −35 regulatory region from the trp promoter and the −10 regulatory region from the lac promoter. Most preferably, the promoter is one in which the −35 trp consensus sequence is located about 17 nucleotides upstream from the −10 lac consensus sequence.

The transcriptional regulatory region may additionally include regulatory sequences which allow the time of expression of the gene of interest to be modulated, for example by presence or absence of nutrients or expression products in the growth medium, temperature, and the like. For example, expression of the gene of interest may be regulated by temperature of the host cell growth medium by including a regulatory sequence comprising the bacteriophage lambda $P_L$ promoter, the bacteriophage $O_L$ operator and the gene CI857 which codes for the temperature-sensitive $C_I$ repressor in the expression vector. This would allow regulation of the promoter by interaction between the repressor and the operator at low temperatures, for example about 30° C. Increasing the temperature to about 42° C. would inactivate the repressor and allow expression of the gene of interest.

As an example of modulation using growth-medium nutrients, regulation of the lac or the trp-lac hybrid promoter can be accomplished by use of the gene for the LacI repressor which binds in the lac promoter region downstream from the −10 regulatory region. The LacI repressor gene may be present on an episome, preferably the lacIq enhanced mutant, or can be included in the expression cassette itself. Presence of a significant concentration of the repressor in the growth medium inhibits the promoter function in the absence of inducers. Thus addition of IPTG or lactose to the host cell growth medium enhances promoter function. When the bacterial strain is $Lac^+$, lactose may be used as an inducer instead of IPTG.

The transcriptional regulatory region may additionally include regulatory sequences which terminate transcription and which provide sequences or structures which inhibit degradation of the mRNA and thus increase the stability of the mRNA species and allow for higher expression. Several examples of prokaryotic sequences are known—the trp terminator, the gene 32 (T4) terminator, or synthetic terminators which are similar in sequence to gene 32.

In terms of translational regulation, given the presence of mRNA, expression can be regulated by influencing the rate of initiation (ribosome binding to the mRNA), the rate of elongation (translocation of the ribosome across the mRNA), the rate of post-translational modifications and the stability of the gene product. The rate of elongation is probably affected by codon usage; the use of codons for rare tRNA's may reduce the translation rate. It is therefore preferable to use codons which frequently appear in genes normally expressed by the host cell to increase the translation rate.

Downstream from the −35 and −10 regulatory regions is a consensus nucleotide sequence, generally AGGA, termed the Shine-Dalgarno sequence, which is believed to be involved in ribosomal binding. Optimium ribosomal binding and initiation of translation can be achieved by using a ribosomal binding site functional in the host cell from a highly expressed gene. Evidence also points to the presence of nucleotide sequences surrounding the Shine-Dalgarno sequence and sequences within the coding region which can affect ribosome binding, possibly by the formation of structural motifs through which the ribosome recognizes the initiation site, thus altering nucleotide sequences of the coding region can be used to achieve optimum ribosomal binding and initiation of translation. The sequence of the first about 7 to 30 codons after the initiating codon ATG can also affect binding and expression. Preferably the leader sequence and the Shine-Dalgarno sequence are obtained from the same gene, or where they are obtained from different genes, the codons of the leader sequence can be modified using codon degeneracy to approximate the nucleotide sequence of the natural gene that follows the leader sequence.

The position of the AGGA sequence with respect to the initiating ATG codon can influence expression. Generally the Shine-Dalgarno sequence is located from about 5 to 9 nucleotides from the initiating codon, although, unexpectedly, high levels of expression can be achieved using expression cassettes wherein the Shine-Dalgarno sequence is located from about 10 to 13 nucleotides, preferably 11 to 12 nucleotides from the initiating codon.

Stability of the mRNA is governed by the susceptibility of the mRNA to ribonuclease enzymes. In general, exonuclease digestion is inhibited by the presence of structual motifs at the ends of the mRNA; palindromic structures, altered nucleotides or specific nucleotide sequences. Endonuclease digestion is believed to occur at specific recognition sites within the mRNA and stable mRNA would lack these sites. There is also some evidence that mRNAs undergoing high levels of translation are also protected from degradation by the presence of ribosomes on the mRNA.

Stability of the expression product is aided by expression of the desired gene product as a fused polypeptide in which the desired polypeptide is expressed in conjunction with a second polypeptide or fragment thereof, especially a bacterial polypeptide. Preferably, stability of the expression product is achieved by providing for synthesis of a fusion protein in which the polypeptide of interest is expressed, joined to a leader sequence. A DNA sequence encoding an N-terminal amino acid sequence from, for example, a highly expressed bacterial or bacteriophage gene such as the bacteriophage lambda N protein gene or cro gene or the β-galactosidase gene is joined upstream from and in reading frame with the gene of interest. The leader sequence usually includes from about 8 to about 35, preferably from about 15 to about 25, N-terminal amino acids.

Expression of the polypeptide of interest as a fused protein with a leader sequence from another gene has several advantages in addition to providing for stability. For example, the presence of the N-terminal amino acids provides a means for using general purification techniques for purification of any of a variety of polypeptides. For example, the N-terminal amino acids of the N-protein are predictably antigenic, and thus specific antibodies raised against the N-terminal amino acids of the N-protein may be used for the amino purification of the fusion proteins containing the N-terminus of the N-protein. Furthermore, the N-terminus of the N-protein has a high positive charge, which facilitates purification of the desired protein by ion-exchange chromatography, and the like.

The leader sequence can also be a hydrophobic amino acid sequence, which may additionally function as a signal sequence for secretion. A DNA sequence encoding the signal sequence is joined upstream from and in reading frame with the gene of interest. Typically, the signal sequence includes a cleavage site which is recognized by a signal sequence peptidase. Thus, positioning the polypeptide of interest directly after the signal sequence cleavage site will allow it to be specifically cleaved from the signal sequence and secreted as a mature polypeptide. Examples of hydrophobic amino acid sequences include the bacterial alkaline phosphatase signal sequence; the OMP-A,B,C,D,E or F signal sequences; the LPP signal sequence, β-lactamase signal sequence; and toxin signal sequences.

Other leader sequences which can be used include hydrophilic sequences, for example the N-terminal 41 amino acid residues from amphiregulin which may provide for modification of the function of the polypeptide of interest. In addition, a cytotoxic agent such as a toxin A-chain fragment, ricin A-chain, snake venom growth arresting peptide, or a targeting molecule such as a hormone or antibody can be coupled covalently with the leader sequence with in most cases minimal effect on the biological activity of the gene product of interest. As with the other leader sequences, a DNA sequence encoding the leader sequence is joined upstream from and in reading frame with the gene of interest.

Where the leader sequence is not a signal sequence or does not contain a convenient natural cleavage site, additional amino acids may be inserted between the gene of interest and the leader sequence to provide an enzymatic or chemical cleavage site for cleavage of the leader peptide, following purification of the fusion protein, to allow for subsequent purification of the mature polypeptide. For example, introduction of acid-labile aspartyl-proline linkages between the two segments of the fusion protein facilitates their separation at low pH. This method is not suitable if the desired polypeptide is acid-labile. The fusion protein may be cleaved with, for example, cyanogen bromide, which is specific for the carboxy side of methionine residues. Positioning a methionine between the leader sequence and the desired polypeptide would allow for release of the desired polypeptide. This method is not suitable when the desired polypeptide contains methionine residues.

Where the leader sequence comprises a signal sequence, genes of interest with secretory leader sequences can be expressed with or without the leader sequence under conditions where the sequence may be retained or cleaved. In addition, to obtain a high proportion of the desired polypeptide as a mature, cleaved and refolded peptide secreted into the medium, it is preferable to use a promoter, such as the tac promoter, which can operate at a lower temperature, for example about 30° C. Unexpectedly, higher levels of secretion can be obtained at the lower temperatures. Extremely high expression levels can prevent full translational modifications of the protein to occur, resulting in aggregation and accumulation of uncleaved precursor (i.e., structural protein and secretory leader). Similarly, growth at elevated temperatures, for example 42° C., also tends to result in aggregation and accumulation of uncleaved precursor.

The polypeptide of interest may be any polypeptide for which expression is desired and may be either homologous (derived from the host cell) or heterologous (derived from a foreign source or synthetic DNA sequence). The polypeptide may be derived from prokaryotic sources, or eukaryotic sources, which eukaryotic sources may include fungi, protists, vertebrates, invertebrates, and the like. The polypeptide of interest may include enzymes such as isopenicillin synthetase; mammalian peptides such as interleukins, cytokines, growth factors, e.g. epidermal growth factor, platelet-derived growth factor, oncostatin M, TGF-α and -β, viral growth factors, e.g. Vaccinia Virus, Shopes fibroma; snake venom growth-arresting peptide, brain-derivable peptides, immunoglobulins and fragments thereof, and the like.

Where the gene of interest is to be expressed in a host which recognizes the natural transcriptional and translational regulatory regions of the desired gene of interest, the entire gene with its natural 5' and 3'-regulatory regions may be introduced into an appropriate expression vector. However, where the gene is to be expressed in a host which recognizes the natural transcriptional and translational regulatory regions less well, further manipulation may be required. The non-coding 5'-region upstream from the gene of interest may be removed by endonuclease restriction, Bal31 resection, or the like. Alternatively, where a convenient restriction site is present near the 5'-terminus of the gene of interest, the gene of interest may be restricted and an adapter employed for linking the gene of interest to the promoter region, where the adaptor provides for the lost nucleotides of the gene of interest. A variety of 3'-transcriptional regulatory regions are known and may be inserted downstream from the stop codons.

The DNA sequences encoding the polypeptide of interest can be synthesized using conventional techniques giving overlapping single strands which may be ligated together to define the desired coding sequences. The termini can be designed to provide restriction sites or one or both termini may be bluntended for ligation to complementary ends of an expression vector. For expression of the sequence an initiating methionine is provided. Expression vectors are generally available and are amply described in the literature.

Instead of synthesizing the gene of interest, the gene may be isolated by various techniques. These include isolating mRNA from a host organism which codes for the polypeptide of interest, the mRNA reverse transcribed, the resulting single-stranded (ss) DNA used as a template to prepare double-stranded (ds) DNA and the ds DNA isolated. Another technique is to isolate a piece of the host cell genomic DNA, and using a probe, appropriately degenerate, comprising a region of the most conserved sequences in the gene encoding the polypeptide of interest, identify sequences encoding the polypeptide of interest in the host cell genome. The probe can be considerably shorter than the entire sequence, but should be at least 10, preferably at least 14, more preferably at least 20 nucleotides in length. Longer oligonucleotides are also useful, up to the full length of the gene encoding the polypetide of interest. Both DNA and RNA probes can be used.

In use, the probes are typically labeled in a detectable manner (for example with $^{32}P$-labelled or biotinylated nucleotides) and are incubated with single-stranded DNA or RNA from the organism in which a gene is being sought. Hybridization is detected by means of the label after single-stranded and double-stranded (hybridized) DNA or DNA/RNA have been separated, typically using nitrocellulose paper. Hybridization techniques suitable for use with oligonucleotides are well known to those skilled in the art.

Although probes are normally used with a detectable label that allows for easy identification, unlabeled oligonucleotides are also useful, both as precursors of labeled probes and for use in methods that provide for direct detection of DNA or DNA/RNA. Accordingly, the term "oligonucleotide" refers to both labeled and unlabeled forms.

Once the desired DNA sequence has been obtained it may be manipulated in a variety of ways to provide for expression. For example, chimeric polypeptide sequences may be prepared by combining gene fragments of a least two polypeptides having sequences substantially similiar to naturally occuring polypeptide chains. It is highly desirable that the three dimensional structure of the polypeptide be retained, particularly that portion of the structure which may be responsible for biological activity of the polypeptide of interest. Depending upon the source of the fragments and the length of the desired polypeptide, convenient restriction sites may be designed into the synthetic genes used to construct the chimeric polypeptides. When possible the restriction site(s) leaves the amino acid sequence of the polypeptide unaltered. However, in some cases incorporation of the new restriction site(s) may yield an altered amino acid sequence without changing the activity of the protein.

During the construction of the expression cassette, various fragments of the DNA will usually be cloned in an appropriate cloning vector, which allows for amplification of the DNA, modification of the DNA or manipulation by joining or removing of sequences, linkers, or the like. Normally, the vectors will be capable of replication in at least a relatively high copy number in bacteria. A number of vectors are readily available for cloning in gram-negative bacteria, especially *E. coli,* including such vectors as pBR322, pACYC184, M13, Charon 4A and the like. The cloning vectors are characterized by having an efficient replication system functional in the host bacteria.

The cloning vector will have at least one unique restriction site, usually a plurality of unique restriction sites and may also include multiple restriction sites. In addition, the cloning vector will have one or more markers which provide for selection of transformants. The markers will normally provide resistance to cytotoxic agents such as antibiotics, heavy metals, toxins or the like, complementation of an auxotrophic host, or immunity to a phage. By appropriate restriction of the vector and the cassette, and, as appropriate, modification of the ends, by chewing back or filling in overhangs, to provide for blunt ends, by addition of linkers, by tailing, complementary ends can be provided for ligation and joining of the vector to the expression cassette or component thereof.

After each manipulation of the DNA in the development of the cassette, the plasmid will be cloned and isolated and, as required, the particular cassette component analyzed as to its sequence to ensure that the proper sequence has been obtained. Depending upon the nature of the manipulation, the desired sequence may be excised from the plasmid and introduced into a different vector or the plasmid may be restricted and the expression cassette component manipulated, as appropriate.

In some instances a shuttle vector will be employed where the vector is capable of replication in different hosts requiring different replication systems. This may or may not require additional markers which are functional in the two hosts. Where such markers are required, these can be included in the vector, where the plasmid containing the cassette, two replication systems and the marker(s) may be transferred from one host to another, as required. For selection, any useful marker may be used. Desirably, resistance to neomycin or tetracycline are of interest. However, although a marker for selection is highly desirable for convenience, other procedures for screening transformed cells have been described. See for example G. Reipin et al. *Current Genetics* (1982) 189–193. Transformed cells may also be screened by the specific products they make, for example, synthesis of the desired product may be determined by immunological or enzymatic methods.

The expression cassette may be included within a replication system for episomal maintenance in an appropriate celluar host or may be provided without a replication system, where it may become integrated into the host genome. The DNA may be introduced into the host in accordance with known techniques, such as transformation, using calcium phosphate-precipitated DNA, transfection by contacting the cells with a virus, microinjection of the DNA into cells, and the like.

Once the gene of interest has been introduced into the appropriate host, the host may be grown to express the gene of interest. A variety of prokaryotic hosts may be employed. Host cells can include gram-negative organisms such as *E. coli,* e.g., JM109, JM101, and 107; HB101, DH1 or DH5. Particularly suitable are gram-positive organisms such as *B. subtilis* which have no periplasmic space and directly secrete polypeptides into the growth medium.

The host cell may be grown to high density in an appropriate nutrient medium. Where the promotor is inducible, permissive conditions will then be employed, for example, temperature change, exhaustion or excess of a metabolic product or nutrient, or the like. For example, where the regulatory sequence comprises the bacteriophage $\lambda P_L$ promoter, the bacteriophage $O_L$ operator, and the CI857 temperature sensitive repressor, the host cells may be grown at the permissive temperature, generally about 30° C., at which temperature transcription from the $P_L$ promoter is repressed and the host cells may grow unhindered by the demands of the synthesis of the foreign gene product, which additionally may be toxic to the host organism. When the host cells have reached an optimal density, the temperature may be increased to a non-permissive temperature, for example about 42° C., at which time the CI repressor is rendered inactive, permitting transcription from the $P_L$ promoter.

Maximal secretion can be obtained by using the lac promoter or a trp-lac promoter and induction with a metabolic inducer such as lactose for a $lac^+$ host strain, and providing $lacI^q$ on a vector. Examples of host cells which could be used with this system include DH1, DH5 or HB101.

Where the product is retained in the host cell, the cells are harvested, lysed and the product isolated and purified by extraction, precipitation, chromatography, electrophoresis, and the like. Where the product is secreted into the periplasmic space, the cells are harvested and the product is liberated by destruction of the cell wall, e.g., by hypotonic shock and the like. Where the product is secreted into the medium, the nutrient medium may be collected and the product isolated by conventional means, for example, affinity chromatography. To produce an active protein it may be necessary to allow the protein to refold. If the protein is expressed as a fusion protein with the leader sequence, the leader sequence may be removed by treatment with for example formic acid or cyanogen bromide. The leader sequence preferably is removed after refolding of the protein.

The following examples are offered by way of illustration and not by way of limitation.

EXPERIMENTAL

Table of Contents

Biological Deposits
Methods

Example I

Activity Assays

A. Mitogenic Assay
B. Soft Agar Colony Growth Stimulation Assay
C. EGF Receptor Binding Inhibition Assay
D. Wound Healing
 1. Mid-Dermal Thermal Injuries
 2. Mid-Dermal Donor Graft Injuries
E. Inhibition of DNA Synthesis
F. Inhibition of Tumor Growth in Nude Mice Example II Construction of Cloning and Expression Plasmids A. Plasmid pBM11
 1. Construction of pBM4
 2. Construction of pBM8
 3. Construction of pBM9
 4. Construction of pBM10
 5. Final Construction of pBM11
B. Construction of pBM11/M4
 1. Construction of pBM11/M
 2. Construction of pBM11/M1
 3. Construction of pBM11/M2
 4. Construction of pBM11/M3
 5. Final Construction of pBM11/M4
C. Construction of pBM11M5
D. Construction of pBM11/C Series
E. Construction of pBM11/NDP
F. Construction of pBM16t
G. Construction of pBM16/NDP
H. Construction of pBM11/PAD (also called pBM11M3/PAD)
I. Construction of pBM14
 1. Construction of pBM12
 2. Construction of pBM13
 3. Final Construction of pBM14
J. Plasmid pLEBam
K. Plasmid plac/cro-βgal
L. Plasmid ptac/cro-βgal
M. Plasmid TacPak
N. Plasmid pTCPt
O. Plasmid pTNPt
 1. Preparation of pBM16t
 2. Preparation of the 2.8 kb EcoRI-BamHI fragment of pBM16t/VGFa lacking the HindIII site
 3. Preparation of the 150 bp BamHI-BsmI fragment of pBM11/PAK
 4. Preparation of oligonucleotides TacA+ and TacA−
 5. Ligation and Isolation of pTNPt Example III Preparation of Genes of Interest A. Synthetic Growth Factor Genes
 1. TGF Synthetic Oligonucleotides
 2. VGF Synthetic Oligonucleotides
 3. EGF Synthetic Oligonucleotides
 4. Assembly Growth Factor Genes
B. Synthetic Platelet Factor 4 Gene
C. DNA Cloning of Oncostatin M
 1. Preparation of cDNA Libraries
 2. Restriction Site Mapping
 3. DNA Sequence of Oncostatin M
 4. RNA Analysis Example IV Expression of the Polypeptide of Interest as a Fusion Protein with the N-Protein A. Modified Synthetic TGF
 1. Preparation of pBM11/N/TGF
B. Modified Synthetic TGF-VGF Hybrid
 1. Preparation of pBM11/N/TTV
C. Synthetic Platelet Factor 4
 1. Preparation of pBM11/N/PF4

Example V

Expression of the Polypeptide of Interest as a Fusion Protein with the N-Protein and a Cleavage Site A. Modified Synthetic VGF
 1. Preparation of pBM11/NDP/VGFA
 2. Preparation of pBM11/NDP/VGFa
B. Modified Synthetic TGF-VGF Hybrids
 1. Preparation of pBM11/NDP/TTV
 2. Preparation of pBM11/NDP/VTV
 3. Preparation of pBM16/NDP/TVV
C. Synthetic EGF
 1. Preparation of pBM11/NDP/EGF
D. Synthetic Platelet Factor 4 (PF4)
 1. Preparation of pBM11/NDP/PF4
E. Oncostatin M
 1. Construction of pBM16/NDP/OncoM
 2. Preparation of pBMX/OncoM Example VI Expression of the Polypeptide of Interest As a Fusion Protein with the Modified Alkaline Phosphatase Signal Sequence A. Preparation of pBM11/PAD/EGF
 1. Preparation of 0.17 kb EcoR I-BamHI fragment of EGF
 2. Preparation of 0.5 kb Pvu I-Hind III fragment of pBM11/PAD
 3. Preparation of the 5.2 kb Pvu I-BamHI fragment of pBM11/PAD
 4. Ligation and isolation of pBM11/PAD/EGF
B. Preparation of pBM11/PAD/OncoM
 1. Preparation of modified Oncostatin M gene fragment
 2. Preparation of pBM11M3/PAD fragments
 3. Ligation and isolation of pBM11/PAD/OncM
C. Preparation of pBM11/PAD/nVGFa
 1. Preparation of 0.5 kb HindIII-PvuI digested pBM11/PAD
 2. Preparation of the 5.2 kb PvuI-BamHI pBM11 plasmid fragment
 3. Preparation of the 170 bp NcoI(blunt)-BamHI synthetic VGFa gene
 4. Ligation and isolation of pBM11/PAD/nVGFa
D. Preparation of pBM11/PAD/PF4

Example VII

Expression of the Polypeptide of Interest as a Fusion Protein with the Alkaline Phosphatase Signal Sequence A. Preparation of pBM11/PAK/nVGFa
B. Preparation of pBM11/PAK/EGF
C. Preparation of TacPak/EGF Example VIII Expression of the Polypeptide of Interest as a Fusion Protein with the Alkaline Phosphatase Signal Sequence Using an Expression Cassette Comprising a Transcriptional Termination Region A. Preparation of pTCPt/EGF
 1. Preparation of the 420 bp HindIII(blunt)-BamHI fragment of TacPak/EGF
 2. Preparation of the 2.8 kb EcoRI(blunt)-BamHI fragment of pBM16t/NDP/VGFa
 3. Ligation and Isolation of pTCPt/EGF
B. Preparation of pTCPt/nVGFa
 1. Preparation of the 350 bp PvuI-BamHI fragment of pBM11/PAK/nVGFa
 2. Preparation of the 2.8 kb PvuI-BamHI fragment of pTCPt/EGF
 3. Ligation and Isolation of pTCPt/nVGFa
C. Preparation of pTNPt/EGF
 1. Preparation of 2.8 kb PvuI-BamHI pTNPt
 2. Preparation of 300 bp PvuI-BamHI fragment of pBM11/PAK/EGF
 3. Ligation and Isolation of pTNPt/EGF Example IX Isolation of Recombinant Polypeptides A. Growth Factors Produced in pBM-Based Vectors Using the PL Promoter and the ts CI Repressor
 1. TGF and Modified TGF
  a. N/TGF
 2. Modified and Truncated VGF
  a. PAD/nVGFa
  b. NDP/VGFa
  c. VGFa
  d. NDP/VGFA
 3. Chimeric TGF/VGF Hybrids
  a. N/TTV
  b. NDP/TTV
  c. NDP/VTV
  d. NDP/TVV
B. Growth Factors Produced in Vectors Comprising the tac or lac Promoters
 1. PAK/EGF
 2. PAK/nVGFa
C. Platelet Factor 4
 1. N/PF4
 2. NDP/PF4
D. Oncostatin M
 1. NDP/Oncostatin M
 2. PAD/Oncostatin M Example X Biological Activity of Recombinant Growth Factors Prepared in Prokaryotic Cells A. EGF Receptor Binding
 1. Receptor Binding of Chimeric Peptides
B. Mitogenic Activity C. Wound Healing 1. Mid-Dermal Injuries 2. Mid-Dermal Donor-Graft Injuries Example XI Biological Activity of Recombinant Platelet Factor 4 Prepared in Prokaryotic Cells A. Inhibition of DNA Synthesis B. Inhibition of Growth of Tumors in Nude Mice Example XII Biological Activity of Recombinant Oncostatin M Prepared in Prokaryotic Cells A. Physicochemical Characterization

1. SDS-PAGE

B. Growth-Inhibitory Activity of Recombinant Oncostatin M

C. Receptor Binding Activity of Recombinant Oncostatin M

Biological Deposits

The following expression plasmids, all transformed into *E. coli* HB101, were deposited on the indicated date with the American Type Culture Collection, 12301 Parklawn Drive, Rockville, Md. 20852 and have the identification and ATCC Designations given below:

| IDENTIFICATION | ATCC DESIGNATION | DATE OF DEPOSIT |
|---|---|---|
| pBM11 | 67366 | |
| pBM14 | 67367 | |
| pBM11/PA/VGF | 67417 | June 3, 1987 |
| pBM11/DP/VGFa | 67418 | June 3, 1987 |
| pBM11/PA/EGF | 67419 | June 3, 1987 |
| pBM11/M5 | 67436 | |
| pBM11/C2 | 67437 | |
| pBM11/NDP/EGF | 67547 | October 23, 1987 |

Methods

General cloning techniques were used as described in Maniatis et al., 1982 "Molecular Cloning: A Laboratory Manual",Cold Spring Harbor Laboratory, CSH, N.Y. All DNA-modifying enzymes were obtained from commercial suppliers. They were used according to the manufacturers instructions. Materials and apparatus for DNA purification and separation were used according to instructions from the supplier.

EXAMPLE I

Activity Assays

A. Mitogenic Assay

The mitogenesis assays were performed as follows: Diploid human fibroblasts obtained from explants of newborn foreskin were seeded at a density of $3\times10^4$ cells/well (96-well plates, Nunclon, Roskilde, Denmark) and were grown to confluency in Dulbecco's modified Eagle's medium (GIBCO)/10% newborn calf serum. Cultures were then placed in medium containing 0.2% newborn calf serum, and two days later various concentrations of the growth factor to be tested were added. After 8 hrs, cultures were labeled with 5-[$^{125}$I]iodo-2'-deoxyuridine (Amersham, 10 $\mu$Ci/ml, 5 Ci/mg; 1 Ci=37 GBq), and the amount of isotope incorporated into TCA insoluble material was determined as described (Twardzik et al., *Proc. Natl. Acad. Sci. USA* (1985) 182:5300–5304).

B. Soft Agar Colony Growth Stimulation Assay

A 0.5 ml base layer of 0.5% agar (Agar Noble; Difco Laboratories, Detroit, Mich.) in growth medium was added to 24-well Costar tissue cluture plates. One-half ml 0.3% agar in growth medium containing 1 to $1.5\times10^4$ cells/ml NRK cells or other cell line of interest and various concentrations of the factor to be tested was overlaid on the base layer of agar. The plates were incubated at 37° C. in a humidified atmosphere of 5% $CO_2$ in air and refed after 7 days by addition of 0.5 ml of 0.3% agar in growth medium and containing the same concentration of the factor to be tested. Colonies were counted unfixed and unstained. The number of colonies with greater than 6 cells were scored.

C. EGF Receptor Binding Inhibition Assay

The radioreceptor assays were performed as follows: The binding of $^{125}$I-labeled growth factor to its receptor on monolayers of a target cells was modified from the procedure described by Cohen and Carpenter, *Proc. Natl. Acad. Sci. USA* (1975) 72:1317–1321. Cells ($1\times10^3$ per well) were fixed on 24-well plates (Linbro, Flow Laboratories) with 10% formalin in phosphate-buffered saline prior to assay. Formalin-fixed cells do not slough off plates as easily as do unfixed cells, and replicate values were thus more consistent. Growth factor concentrations are expressed as ng equivalents of the native growth factor/ml i.e., the amount required to produce an inhibition of $^{125}$I growth factor binding equivalent to that produced by a known amount of native growth factor.

D. Wound Healing

1. Mid-dermal Thermal Injuries

Mid-dermal thermal injuries were made on the dorsal thorax of anesthetized female Yorkshire pigs (30 lbs) whose backs had been shaved and depilatated with commercial hair remover cream. A brass template (3x3 cm, 147 gm) was equilibrated in a 70° C. water bath and placed in firm contact with the skin for exactly 10 seconds. The resulting blister was then removed. Five mid-dermal burns were placed on each slide of the spine and were separated from each other by approximately one inch. Burns were treated twice a day with approximately 3 ml of vehicle cream (Silvadene®) alone or containing growth factor or were untreated. After 9 days or 10 days of treatment, the pigs were anesthetized and eschar was removed from the burns. Biopsies were taken of each burn from reepithelialized areas.

2. Mid-dermal Donor Graft Injuries

A 5-month-old 20.5 kg micropig was anesthetized with 20 mg/kg ketamine and 2 mg/kg Rompum. The dorsal thorax was shaved, prepped with betadine and thoroughly rinsed with saline. A series of 6 5x5 cm donor sites were made on each side of the dorsal thorax with a Padgett dermatome at 650/1000 inch by taking two swipes at 30/1000 inch. Topical therapy included 1 ml of saline in 20 gm of Silvadene® distributed evenly between the six wounds on the left side. The right side was treated with 1 ml of the growth factor to be tested, in 20 gm of Silvadene® divided evenly between the six wounds. All wounds were covered with a large burn dressing, chux, ace wrap and gerkin. The animal was anesthetized as described above on post-operative days 1, 2, 3, 4, 7, 8, 9, 10 and 11. The dressings were removed. The wounds were gently wiped with betadine and thoroughly rinsed with saline. The appropriate agent was applied and the wounds were redressed as described above.

E. Inhibition of DNA Synthesis

On day 2 in the morning A549 cells (human lung carcinoma) in Nunc 96-well plates (Kamstrupvej 90. DK-4, 000, Roskilde, Denmark) were set up. These cells were passaged when there were fewer than 30. Into all but the peripheral wells was introduced $4\times10^3$ cells/50 μl/well ($9\times10^4$ cells/ml assay medium (DMEM) with 10% FCS, P/S, glutamine). The peripheral wells received 50 μl PBS and the entire plate was incubated at 37° C. In the afternoon, the test compounds were resuspended in assay medium. All compounds were tested in triplicate. Into each test well was delivered 50 μl of test compound in assay medium, while control wells received 50 μl assay medium alone. Each plate was then incubated at 37° C. for 3 days. On day 4, into each well 50 μl of a solution of $^{125}$I-iodo-2'-deoxyuridine (4 Ci/mg to 0.5 mCi/ml) (1 μl isotope/ml assay medium) was added and the plates incubated at 37° C. overnight. On day 5, the medium was aspirated from the wells, and the wells washed 1× with PBS. One hundred microliters of methanol were added for 10 min at room temperature. The methanol was aspirated and 200 μl of 1 M sodium hydroxide were added to each well. The plate was incubated for 30 min at 37° C., and the sodium hydroxide removed with Titertek plugs (Flow Labs). The plugs were then counted in a gamma counter.

F. Inhibition of Tumor Growth in Nude Mice

Male nude mice (Balb/c-nu+/nu+) were supplied by the Fred Hutchinson Cancer Research Center, Seattle, Wash. At 12 weeks of age, mice were given injections (s.c. in the neck region with approximately $1.3\times10^6$ human lung carcinoma cells (A549) in a volume of 0.2 ml of phosphate-buffered saline. Palpable tumors (approx. 10 $mm^3$) usually developed in 20 days. Each group contained 5 animals. Animals were injected every two or three days at the tumor site with 0.1 ml of PBS (control group) or test sample (1.2 μg/injection) resuspended in 0.1 ml of PBS. Day one post-treatment corresponds to the first day animals were injected at the tumor site with test compounds. Tumor size was measured before subsequent injection on the days indicated and represents the average size of tumor in each animal in the group.

EXAMPLE II

Construction of Cloning and Expression Plasmids

A. Plasmid pBM11

Plasmid pBM11 contains the nucleotide sequence coding for the first 33 N-terminal amino acids of the bacteriophage lambda N protein. It also contains the neomycin resistance gene as a selective marker and a unique BamHI site for cloning of a foreign gene downstream from the lambda PL promotor. pBM11 was constructed as follows.

1. Construction of pBM4

A 2.4 kb DNA fragment containing the gene sequences coding for bacteriophage lambda cI was isolated by digesting (cleaving) 120 ug of lambda cI857S7 DNA (New England BioLabs) with 170 units of Bgl II (BRL) restriction enzyme by incubating the mixture for 2 hr. at 37° C. The digestion mixture was subjected to electrophoresis on a 1% preparative agarose gel using techniques which are conventional in recombinant DNA technology. The 2.4 kb fragment (base pair 35771 to 38103; the numbering is based on Daniel, et al., pg. 519 in Lambda II, ed. by Hendrix, Roberts, Stahl, and Weisber,) was excised from the gel and subjected to electroelution at 100 V for 4 hr. at room temperature. The resulting eluate was recovered, concentrated, and extracted 3 times with an equal volume of phenol:chloroform (1:1). DNA was recovered from the aqueous phase by ethanol precipitation in the presence of 1/10 volume of 3M sodium acetate, pH 5.2. The recovery of the fragment was analyzed by agarose gel electrophoresis Plasmid pPL-lambda (5 ug, Pharmacia) (a pBR322 derivative containing the lambda leftward promoter $P_L$, the lambda N gene and the termination site for transcription of N ($T_L$) and 2 BamHI sites) was digested with 5 units of BamHI by incubating the mixture for 20 min. at 37° C. The digested DNA was separated by agarose-electrophoresis and the full-length DNA was recovered by electroelution using techniques which are conventional in the art.

The linearized $pP_L$-Lambda was treated with alkaline phosphatase to remove the 5' phosphates and ligated to the 2.4 kb BglII fragment of cI857S7 (3 μl, about 250 ng), in the presence of ligase buffer (500 mM Tris-HCl, pH 7.8, 100 mM $MgCl_2$, 200 mM DTT, 10 mM ATP), and T4 DNA ligase (BRL). The resulting reaction mixture was incubated at 12° C. for about 15 hr then used directly for transformation into competent *E. coli* HB101 cells.

*E. coli* cells were made competent by a modification of a procedure described by Hanahan, *J. Mol. Biol.,* (1983) 166: 557–580. A saturated culture of the HB101 cells was diluted 1:200 in Luria Broth supplemented with 20 mM $MgCl_2$ and incubated at 37° C. in a gyratory water bath until the culture reached an optical density (OD) nm $A_{550}$, of 0.3. A 20 ml portion of the culture was harvested by centrifugation at 4° C. The resulting pellet was resuspended in 4 ml of ice cold 50 mM $MnCl_2$/20 mM potassium acetate, pH 6.0 and kept on ice for 15 min. The cells were centrifuged and the pellet was resuspended in 1.4 ml of a solution of 10 mM potassium methanesulfonate, pH 6.2, 100 mM of potassium chloride, 45 mM $MnCl_2$. $4H_2O$, 10mM$CaCl_2$, 3 mM hexamine $CoCl_3$, 100 μl DMSO, and 100 μl 1M DTT.

Three hundred μl of the treated cells were added to 4 μl and 6 μl of the ligation mixture. The treated cells were placed on ice for 30 min., incubated at 42° C. for 90 sec., and then placed on ice again for 90 sec. The cells were then plated on L-Broth agar plates supplemented with 100 μg/ml of ampicillin. As there is no rapid and convenient method to screen for bacterial transformants containing the insert, the transformants were screened by isolating the various DNA by the rapid plasmid DNA isolation procedure of Holmes and Quigley *Anal. Biochem.,* (1981) 114, 193–198. Plasmid DNA preparations from recombinant bacteria which migrate with the "correct" size were further analyzed by restriction map analysis to determine the orientation of the insert.

2. Construction of pBM8

Plasmid pBR322 (5 μg) was digested with PstI (3 ul, New England BioLabs) followed by 3 successive extractions using a 1:1 (v:v) phenol:chloroform solution followed by 2 ether extractions. The DNA was precipitated completeness of digestion was analyzed by electrophoresis on 0.8% agarose gel. The PstI digested pBR322 (10 μl) was treated with T4 polymerase (1 μl, BR1) to convert the 3' protruding ends to blunt ends. A HindIII site was introduced at the PstI site of pBR322 by ligation of a synthetic phosphorylated HindIII* linker (5'-d[CAAGCTTG]) (Pharmacia). The resulting DNA was digested with excess HindIII. Two DNA fragments, a 3.58 Kb fragment and a 782 bp fragment were obtained. The 3.58 Kb fragment was isolated, ligated, and transformed into competent *E. coli* HB101. The transformants were analyzed as described above by sizing the HindIII digested DNA on agarose gels.

3. Construction of pBM9

Plasmid pBM8 was digested with HindIII and BamHI to yield 2 fragments of DNA. The larger fragment, 3.23 Kb, was isolated by agarose gel electrophoresis and recovered by electroelution. Plasmid pNeo (Pharmacia) was digested with HindIII and BamHI to yield a 1.5 Kb fragment containing the gene sequences coding for neomycin resistance. The 1.5 Kb fragment was isolated and purified, then ligated to the 3.23 Kb fragment from pBM8. The resulting plasmid, pBM9, was transformed into competent *E. coli* HB101 and the transformants were screened as described previously.

4. Construction of pBM10

Plasmid pBm9 was digested with NdeI (New England BioLabs). The 5' protruding end was converted to blunt end using *E. coli* DNA Polymerase "Klenow" fragment and ligated to a synthetic phosphorylated EcoRI linker (5'-d [GGAATTCC]-3') at the filled in NdeI site. The resulting plasmid, pBM10, an NdeI site and gained an EcoRI site pBM10 was transformed into competent *E. coli* HB101 and the transformants were screened as described previously.

5. Final Construction of pBM11

Plasmid pBM10 was digested to completion with EcoRI and BamHI. The resulting 2.8 Kb fragment containing the neomycin gene and origin of replication was isolated by agarose gel electrophoresis and recovered by electroelution. Plasmid pBM4 (described above) was digested to completion with EcoRI and BamHI. The 2.84 Kb fragment containing the DNA sequences for the cI gene and lambda $P_L$ promoter and the N gene ribosomal binding site was isolated and recovered. It was then ligated to the 2.84 Kb pBM4 fragment to form pBM11. Plasmid pBMll transformed into competent *E. coli* HB101 and the transformants obtained were screened as described previously. The cells containing pBM11 were screened further by restriction enzyme analysis with BamHI.

B. Construction of pBM11M4

This plasmid was derived from pBM11 and allows a foreign gene to be cloned at a BamHI restriction site directly after the initiating methionine of the N gene. Plasmid pBM11/M4 also contains an NcoI site in the neomycin gene. It was constructed as follows:

1. Construction of pBM11/M

Plasmid pBM11 (20 ug) was cleaved with BamHI and PvuI. After complete digestion, the DNA was electrophoresed through an 0.8% agarose gel and the large fragment (5124 bp) was isolated and recovered by electroelution. A second sample of pBM11 (10 ug) was digested to completion with SphI and the 3' protruding ends converted to blunt ends with T4 DNA polymerase. 0.3 ug of each of the two fragments were mixed together with 37.5 pmol of the phosophorylated synthetic oligodeoxynucleotide (Pharmacia P-L Biochemical)

5' AGGAGAATTCATATGGATCCACAA 3' containing the restriction sites EcoRI, NdeI and BamHI. The resultant plasmid was designated pBM11/M. The plasmid pBM11/M was heated at 100° C. for 3 minutes, then sequentially cooled as follows: 30° C. for 30 minutes, 4° C. for 30 minutes, and 0° C. for 10 minutes. The reannealed DNA was subsequently treated with T4 DNA ligase and transformed into *E. coli* HB101. Neomycin-resistant transformants were screened for plasmids containing the three new restriction sites encoded by the synthetic olignucleotide.

2. Construction of pBM11/M1

Plasmid pBM11/M was digested to completion with BamHI then electrophoresed through a 0.7% agarose gel. The large fragment (5554 bp) was isolated and recovered by electroelution. The resultant plasmid, which lacks the 100 bp region of the lambda N gene downstream from the ribosomal binding the translation initiation site, was designated pBM11/M1. Plasmid pBM11/M1 was religated and transformed into competent *E. coli* HB101.

3. Construction of pBM11/M2

A first sample of plasmid pBMll (0.3 ug) was cleaved with BamHI and PvuI. A second sample of plasmid pBM11 (0.3 ug) was cleaved with SphI and then treated with T4 polymerase. The two samples were combined with 3.75 pmol of the phosphorylated synthetic oligodeoxynucleotide (Pharmacia P-L Biochemical)

5' AGGAGAATCCAGATGGATCCACAA 3' which contains only a BamHI. The mixture was heated and cooled as described previously, and treated with T4 DNA ligase and *E. coli* DNA polymerase "Klenow" fragment. The resultant plasmid, designated pBM11/M2, was transformed into competent *E. coli*=HB101. Neomycin-resistent colonies were screened for plasmids containing the new BamHI site encoded by the synthetic oligodeoxynucleotide.

4. Construction of pBM11/M3

Plasmid pBM11/M2 was digested to completion with BamHI. The cleaved DNA was electrophoresed through a 0.7% agarose gel and the large fragment (5554 bp) isolated and recovered by electroelution. The DNA religated and designated pBM11/M2 transformed into competent *E. coli* HB101.

5. Final Construction of pBM11/M4

Plasmid pBM11/M1 (20 ug) was digested to completion with EcoRI and BamHI, then electrophoresed through a 0.7% agrose gel. The large fragment (5544 bp) was isolated and recovered by electroelution. This DNA was ligated to the following pair of phosphorylated synthetic oligodeoxynucleotides (200 pmol each):

5' AATTCCCATGGGG 3' and

3' GGGTACCCCTAG 5' which contains a NcoI site. The mixture was heated to 65° C. and allowed to cool to 25° C. in order to anneal. The resultant plasmid designated pBM11/M4, was transformed into competent *E. coli* HB101. Neomycin resistant colonies were screened for plasmids containing a new NcoI site.

C. Construction of pBM11/M5

Plasmid pBM11/M5 was derived from pBM11. An NcoI site present in the neomycin resistant gene has been removed by self directed mutagenesis. Plasmid pBM11/M5 is identical to pBM11/M4 except that the NcoI site in the neomycin gene has been removed by site-specific mutagenesis. Cloning of foreign genes into pBM11/M5 therefore does not require partial digestion of the vector with NcoI.

D. Construction of pBM11/C Series

A pBM11 plasmid containing the *E. coli* consensus ribosomal binding site was produced and designated "pBM11/C." Plasmid pBM11, 30 ug, was digested with 80 ug PvuI and 192 units BamHI. The resulting two fragments (5.1 kb and 0.53 kb) were separated by gel electrophoresis and isolated by electroelution. The 0.53 kb fragment was then digested with HaeIII. The resulting fragments were separated by gel electrophoresis and the 324 bp fragment was isolated by electroelution. The construct pBM11C, the 5.1 kb, the 324 bp fragments isolated from plasmid pBM11 and a phosphorylated chemically synthesized linker,

5' GTAAGGAGGTTTAATATTATG 3'

3' CATTCCTCCAAATTATAATACCTAG 5', were ligated together. The plasmid thus constructed is termed pBM11/C. Plasmid pBM11/C has restriction site BamHI as the cloning site as well as a unique SspI restriction site within the spacer region of the ribosomal binding site. It has been reported that spacer length affects the efficiency of protein translation. The presence of the SspI site allows the length of the spacer region to be changed and also allows for the insertion of other cloning sites for other genes to be expressed.

Modification of plasmid pBM11/C has also been performed. pBM11/C, 10 ug, was digested with restriction enzyme SspI, 45U, and the 5'phosphate was removed by phosphatase. This DNA was ligated to a phosphorylated synthetic NcoI linker CCATGG. The resulting plasmid, termed pBM11C/1, contains 2 NcoI sites, one in the neomycin gene and one for the cloning of the foreign gene(s). To avoid performing NcoI partial digestion of pBM11/C1 in the cloning of foreign gene(s), the NcoI restriction site in the neomycin gene was removed by site-specific mutagensis using techniques described previously. This plasmid is termed pBM11/C2.

E. Construction of pBM11/NDP

Plasmid pBM11/NDP, derived from plasmid pBM11, contains the nucleotide sequences coding for the first 32 amino acids of the lambda N protein followed by nucleotide sequences coding for the acid cleavable aspartic acid-proline dipeptide. The plasmid contains an NcoI site and a ClaI site for cloning a foreign gene downstream of the $P_L$ promoter.

F. Plasmid pBM16t

This plasmid is identical to pBM11/NDP except that it lacks the NcoI site in the neomycin gene as described above (Example II.F.) and it contains the transcription terminator as described for plasmid pTNPt (see Example (II.N. for terminator sequence).

G. Construction of Plasmid pBM16/NDP

Plasmid pBM11/NDP/VGFa (see Example V.A.1. below) was digested with NcoI and BamHI which removes the synthetic gene TVV from the pBM16/DP plasmid fragment. The pBM16/NDP NcoI-BamHI 5.5 kb plasmid fragment was then gel purified. The NcoI site in this fragment is positioned downstream of the nucleotide sequences coding for the first 32 amino acids of the N-gene and directly after the sequences coding for the acid labile dipeptide Asp-Pro.

H. Construction of pBM11/PAD (Also Called pBM11M3PAD)

This plasmid is derived from pBM11/M3 and allows a foreign gene to be cloned at a HindIII, SmaI or BamHI site downstream from a modified alkaline phosphatase signal sequence. Synthetic oligonucleotides were designed to allow insertion of DNA coding for a modified alkaline phosphatase signal peptide and a linker region with 3 cloning sites (HindIII, SmaI and BamHI) into the pBM11 expression vector downstream from the $P_L$ promoter and N gene ribosomal binding site. The nucleotide sequence was optimized to be as similar as possible to the nucleotide sequence of the amino terminus of the lambda N gene as the lambda N gene sequence has evolved with that of its ribosomal binding site for efficient ribosome initiation and translation.

The sequences of the oligonucleotides coding for the signal sequence are shown below.

PA1 5' GATCAATCTACAATCGCCCTCGCACT-
TCTCCCACTGCTGTTCACTCCAGTGA-
CAAAAGCTTCCCGGG 3'

PA2 5' GATCCCGGGAAGCTTTTGTCACTGGAGT-
GAACAGCAGTGGGAGAAGTGCGAGGGCGATTGTAGATT
3'

Oligonucleotides A1 and A2 were synthesized on a Applied Biosystems Oligonucleotide Synthesizer and purified on an acrylamide gel. The oligonucleotides were phosphorylated at the 5' end using T4 polynucleotide kinase and then annealed to each other yielding a double stranded 0.067 kb DNA fragment with a BamHI overhang at each end.

pBM11/PAD was constructed as follows:

Plasmid pBM11/M3 (20 ug) was digested with 30 units of BamHI to linearize the plasmid directly after the N gene ribosomal binding site and the ATG codon for the initiating methionine. The 5' phosphates were removed by digestion with calf intestinal alkaline phosphatase.

The 0.067 kb PA oligonucleotide fragment was ligated to the linearized pBM11/M3 plasmid and the resulting DNA was used to transform competent *E. coli* HB101. The transformants were screened by nucleotide sequencing, and a correct construct was isolated.

I. Construction of pBM14

1. Construction of pBM12

Plasmid pBR322 was digested with restriction enzyme PstI. The resulting 3' protruding end was converted to a blunt end by treating the digestion product with T4 DNA polymerase according to conventional techniques. Synthetic BglII linker (5'-d[CAGATCTG]) was phosphorylated and ligated onto the blunt end DNA and used to transform competent *E. coli* HB101. Plasmid DNA preparations were prepared from tetracycline-resistant transformants using conventional techniques digested with PstI and BglII to screen for loss of the PstI restriction site and addition of the BglII restriction site.

2. Construction of pBM13

Plamid pBM4, obtained as described above, was digested with HpaI. The 3' protruding end was converted to a blunt end and the phosphorylated BglII linker added to the blunt end. The ligation reaction mixture was used to transform competent *E. coli* HB101.

3. Final Construction of pBM14

Plasmid pBM12 was digested with BglII and EcoRI. The resulting 3.6 Kb fragment containing the tetracycline gene and origin of replication was isolated and recovered. Plasmid pBM13 was digested with BglII and EcoRI and the resulting 2.8 Kb fragment containing the bacteriophage lambda cI857 DNA sequences and the lambda $P_L$ and the N ribosomal binding site was isolated and recovered. The 3.6 Kb fragment from pBM12 and 2.8 Kb fragment from pBM13 were ligated to form plasmid pBM14. The resulting ligation mixture was transformed into *E. coli* HB101 and the resulting transformants screened for pBM14. The putative pBM14 was analyzed further by restriction digest using conventional techniques.

J. Plasmid pLEBam

Plasmid pLEBam was used to clone synthetic oligonucleotide fragments because of its convenient BssHII and BamHI restriction sites. A plasmid with NcoI and BamHI restriction sites such as pBM11 or pBM11/NDP (described below) can be used for cloning the synthetic nucleotide fragments.

K. Plasmid plac/cro-β gal

The controlling elements of the vector plac/cro-β gal consist of the operator-promoter region of *E. coli* lactose (lac) operon, as well as the ribosome-binding sites of lac and cro. This vector is derived from plasmids pTR213 (Roberts et al., *Proc. Natl. Acad. Sci. USA* (1978) 76:760) and pLG300 (Guarante et al., *Cell* (1980) 20:543).

Plasmid plac/cro-β gal was constructed by ligating a 0.96 kb PstI-BglII fragment from pTR213 and a 5.54 kb PstI-BamHI fragment from pLG300 in the presence of the oligonucleotide linker which had been digested with BamHI and BglII:

AAAGATCTCAGGCCTCGAGGATCC

TTTCTAGAGTCCGGATCTCCTAGG

This linker served the following purposes: (1) to regenerate the BglII and BamHI sites from the parental plasmids, (2) to provide additional sites for the insertion of foreign DNA, and, (3) to allow the inserted DNA to be in the correct translational reading frames with respect to the cro 5'-gal coding sequence.

L. Plasmid ptac/cro-βgal

Plasmid ptac/cro-βgal allows a foreign gene to be cloned downstream of the N-terminal 21 amino acids of the bacterial Cro protein. It was constructed by inserting a 0.87 kb RsaI fragment of the plac/cro-βgal plasmid into pDR540 (Pharmacia) at the BamHI site, which was previously converted to blunt ends by the action of Klenow enzyme. The orientation of the inserted DNA was such that the ribosomal binding site and the coding sequence of Cro were located downstream from the ribosomal binding site of lac. The resulting plasmid, ptac/cro, contained ribosomal binding sites of both lac and cro, and the N-ter,minal coding sequences of Cro.

The second step in the construction of ptac/cro-βgal was to ligate the 1.16 kb and the 5.54 kb PstI-BamHI fragments from ptac/cro and pLG400 plasmids, respectively. Expression vector ptac/cro-βgal is thus similar to plac/cro-βgal, with the exception that the promoter of ptac/cro-βgal consists of the −35 region from the promoter of the tryptophan operon and the Pribnow box (−10 region) of the lac operon. This hybrid promoter allows a higher level of expression than plac/cro-βgal.

M. TacPak

For preparation see Example VII c.

N. Plasmid pTCPt

This plasmid is designed to have the tac promoter elements and utilize the cro SD to express the gene of interest behind the alkaline phosphatase signal sequence. An example of the construction of this plasmid is given below in the construction of pTCPt/EGF.

O. Construction of pTNPt ([trp-35]17 bp[lac-10][nSD]8 bp[ATG]/Alkaline Phosphatase Signal/linker/trans. term.-NEO)

This plasmid is designed to have the tac promoter elements and utilize the N-gene SD to express a given gene behind the alkaline phosphatase signal sequence. It has a pBR322 background with the Neomycin resistance gene. Plasmid pTNPt was constructed as follows:

1. Preparation of the 2.8 kb EcoRI-BamHI Fragment of pBM16t/VGFa Lacking the HindIII Site Plasmid pBM16 t/VGFa was digested with EcoRI and BamHI and the 2.8 kb fragment was isolated. The 2.8 kb fragment was ligated to an EcoRI-BamHI linker and a correct construct was isolated by restriction analysis and is referred to as Intermediate I.

The unique HindIII site near the Neomycin resistance gene was removed from the Intermediate I plasmid by digestion with HindIII, creating blunt ends using Klenow fragment, and religating. This resulted in Intermediate II plasmid which lacked the HindIII site.

The 2.8 kb EcoRI-BamHI fragment of pBM16t/VGFa lacking the HindIII site was isolated by digesting pIntermediate II with EcoRI and BamHI. The resulting 2.8 kb fragment was isolated by agarose gel electrophoresis.

2. Preparation of the 150 bp BamHI-BsmI Fragment of pBM11/PAK

Plasmid pBM11/PAK is identical to pBM11/PAK/EGF except that it contains a linker region with HindIII, SmaI and BamHI sites downstream of the alkaline phosphatase signal sequence instead of the EGF gene. pBM11/PAK was digested with BsmI and BamHI and the 150 bp fragment containing the N-gene SD, the alkaline phosphatase signal sequence and the linker region was isolated.

3. Preparation of Oligonucleotides TacA+ and TacA−

Oligonucleotides TacA+ and TacA− were synthesized on an Applied Biosystems Oligonucleotide synthesizer and were designed to have an EcoRI overhang at the 5' end with the trp-35 consensus sequence separated from the lac-10 consensus sequence by 17 nucleotides within which was positioned a SstI site. The sequence also contained the 5' end of the lac mRNA, the lac repressor binding site and a BsmI overhang.

TacA+ 5'AATTACTCCCCATCCCCCTGTTGACAAT-TAATCATCGAGCTCGTATAATGTGTG-GAATTGTGAGCGGATAACAATTTCACACAG 3'

TacA− 5'GTGTGAAATTGTTATCCGCTCACAATTC-CACACATTATACGAGCTCGATGATTAAT-TGTCAACAGGGGGATGGGGAGT 3'

4. Ligation and Isolation of pTNPt

The 2.8 kb EcoRI-BamHI fragment, the 150 bp BsmI-BamHI fragment and oligonucleotides TacA+ and TacA− were ligated together using DNA ligase and the DNA was used to transform competent JM109(lacIq). A correct construct was isolated by restriction analysis and DNA sequencing.

```
                                           (EcoRI site of pBM11)
                                                     |
                                                     GAATTACTCCCCATCC

                            SstI
       trp-35       (17bp)         lac-10
CCCTG [TTGACA] ATTAATCATCGAGCTCG (TATAATG)

                                         BsmI
     5'lac mRNA->                       n mRNA->
TGTGG/AATTGTGTGAGCGGATAACAATTTCACACAGCATTCAAAGCAGAAGGCT

TTGGGGTGTGTGATACGAAACGAAGCATTGGCCGTAAGTGCGATTCCGGATTAGC

TGCCAATGTGCCAATCGCGGGGGGTTTTCGTTCAGGACTACAACTGCCACACACC

                                                   PvuI
                 nSD     (8bp)  Signal Sequence ->
ACCAAAGCTAACTGAC {AGGA} GAATCCAG ATGAAACAATCTACGATCGCCC
                                 M  K  Q  S  T  I  A  L

                                              SmaI
                                         HindIII      BamHI
TCGCACTTCTCCCACTGCTGTTCACTCCAGTGACAAAAGCTTCCCGGGATCCGTG
  A  L  L  P  L  L  F  T  P  V  T  K

                                    (BamHI site of pBM11)
           Trans. Term.                          |
ACTAATTGGGGACCCTAGAGGTCCCCTTTTTTATTTTAAAACGATCC
```

EXAMPLE III

Preparation of Genes of Interest

A. Synthetic Growth Factor Genes

Synthetic growth factor genes were designed which use host cell codons optimized for high levels of expression. In addition, several convenient restriction sites were designed into the synthetic genes. When possible, the new restriction sites left the amino acid sequence of the growth factor gene unaltered, however, in some cases incorporation of the new restriction site yielded an altered amino acid sequence. These sites roughly divide the synthetic genes into thirds yielding N-terminal, middle and C-terminal domains.

The natural VGF gene product contains an extreme N-terminal domain which has no counterpart in mature TGF. VGF fragments lacking this domain are referred to as truncated. The restriction sites were used for initial construction of the final genes from partial synthetic oligonucleotide fragments extending from one restriction site to another. The oligonucleotides were synthesized on an Applied Biosystems oligonucleotide synthesizer and were purified on an acrylamide gel. The oligonucleotides were phosphorylated at the 5' end using T4 polynucleotide kinase and each oligonucleotide was then annealed to its complement.

1. TGF Synthetic Oligonucleotides a. Human TGF N-terminal domain

```
             TGF ->
   BssHIINcoI
        M  V  V  S  H  F  N  D  C  P  D  S  H  T  Q  F
5' CGCGCCATGGTTGTTTCTCACTTTAACGACTGCCCGGACTCTCATACTCAGT
3'      GGTACCAACAAAGAGTGAAATTGCTGACGGGCCTGAGAGTATGAGTCA

     KpnI
  C  F  H  G  T
TTTGCTTTCATGGTAC 3'   TGF104
AAACGAAAGTAC     5'   TGF103
```

b. Modified human TGF middle domain with the human sequence QEDK being altered to QEEK, the sequence found in rat TGF

```
   KpnI                                      SphI
        C  R  F  L  V  Q  E  E  K  P  A  C
5'      CTGCCGTTTTCTGGTTCAGGAAGAAAAACCGGCATG 3'  TGF101
3' CATGGACGGCAAAAGACCAAGTCCTTCTTTTTGGCC      5'  TGF102
```

c. Human TGF C-terminal domain:

```
   SphI
        V  C  H  S  G  Y  V  G  A  R  C  E  H  A  D  L
5'      CGTTTGCCATTCTGGCTACGTTGGCGCACGTTGCGAACACGCTGACCT
3' GTACGCAAACGGTAAGACCGATGCAACCGCGTGCAACGCTTGTGCGACTGGA

          BamHI
 L  A  Ter
GCTGGCTTAAG     3'  TGF205
CGACCGAATTCCTAG 5'  TGF206
```

2. VGF Synthetic Oligonucleotides a. VGF extreme N-terminal domain

```
   HindIII
    E  D  S  G  N  A  I  E  T  T  S  P  E  I  T  N  A
5' AGCTGACTCTGGTAACGCTATCGAAACTACTTCTCCGGAAATCACTAACGCT
3'      CTGAGACCATTGCGATAGCTTTGATGAAGAGGCCTTTAGTGATTGCGA

T  T
ACTACT 3'  VGF105
TGATGA 5'  VGF106
```

b. Modified VGF N-terminal domain including Asp-Pro cleavage site, with the sequence HGT replacing the natural sequence HGD

```
    BamHI
     I  D  P  M  D  I  P  A  I  R  L  C  G  P  E  G  D
5' GATCGATCCCATGGACATCCCGGCTATCCGTCTGTGCGGCCCGGAAGGCGAC
3'     CTAGGGTACCTGTAGGGCCGATAGGCAGACACGCCGGGCCTTCCGCTG

G  Y  C  L  H  G  T
GGCTACTGCCTGCATGGTAC 3'  VGF104a
CCGATGACGGACGTAC     5'  VGF103a
```

c. Modified VGF middle domain having the sequence GYAC replacing the natural sequence GMYC

```
    KpnI                                 SphI
      T  C  I  H  A  R  D  I  D  G  Y  A  C
5'     CTGCATCCATGCACGTGACATCGACGGCTACGCATG 3'  VGF101a
3' CATGGACGTAGGTACGTGCACTGTAGCTGCCGATGC     5'  VGF102a
```

d. VGF C-terminal domain, 5' end

```
   SphI                          EcoRI
     C  R  C  S  H  G  Y  T  G
5'     CCGTTGCTCTCATGGCTACACTGG      3'  VGF1A
3' GTACGGCAACGAGAGTACCGATGTGACCTTAA 5'  VGF2A
```

e. Modified VGF C-terminal domain, 5' end, with the sequence VCS replacing the natural sequence RCS

```
    SphI                          EcoRI
          V  C  S  H  G  Y  T  G
5'     CGTTTGCTCTCATGGCTACACTGG      3'  VGF1
3' GTACGCAAACGAGAGTACCGATGTGACCTTAA 5'  VGF2
```

f. VGF C-terminal domain, 3' fragment, ending at YQR instead of PNT, the deduced C-terminus of natural secreted VGF

```
    EcoRI
     I  R  C  Q  H  V  V  L  V  D  Y  Q  R  Ter
5' AATTCGTTGCCAGCATGTTGTTCTGGTCGACTACCAGCGTTAAG
3'     GCAACGGTCGTACAACAAGACCAGCTGATGGTCGCAATTC

BamHI
GATC 3'  VGF3
     5'  VGF4
```

3. EGF Synthetic Oligonucleotides

Three sets of overlapping synthetic oligonucleotides 1(A, B), 2(A,B) and 3(A,B) coding for human EGF were synthesized on an Applied Biosystems oligonucleotide synthesizer and purified on an acrylamide gel. The oligonucleotides were phosphorylated at the 5' end using T4 polynucleotide kinase. Each oligonucleotide was annealed to its complement.

```
   NcoIEcoRI
    M  N  S  D  S  E  C  P  L  S  H  D  G
5' CATGAATTCTGACTCTGAATGCCCGCTGTCTCATGACGGC
3'     TTAAGACTGAGACTTACGGGCGACAGAGTACTGCCG

           Y
           TAC       3'  EGF1A
           ATGACGGAC 5'  EGF2A

                 NsiI
   C  L  H  D  G  V  C  M  Y  I  E  A  L  D  K  Y  A
5' TGCCTGCATGACGGCGTATGCATGTACATCGAAGCTCTGGACAAGTACG
3'       GTACTGCCGCATACGTACATGTAGCTTCGAGACCTGTTCATGC

           SphI
             C
           CATG 3'  EGF1B
                5'  EGF2B

SphI
        N  C  V  V  G  Y  I  G  E  R  C  Q  Y  R  D
5'     CAACTGCGTTGTTGGCTACATCGGCGAACGTTGCCAGTACCGTGAC
3' GTACGTTGACGCAACAACCGATGTAGCCGCTTGCAACGGTCATGGCACTG

                                 BamHI
           L  K  W  W  E  L  R  *
           CTGAAATGGTGGGAACTGCGTTAAG     3'  EGF3
           GACTTTACCACCCTTGACGCAATTCCTAG 5'  EGF4
```

4. Assembly of Growth Factor Genes a. Preparation of Plasmid pLEBam/TTV

The synthetic chimeric growth factor, denoted TTV or (TGF/TGF/VGF) was assembled in the cloning vector pLE-Bam. This hybrid growth factor contained the amino acid sequence of human TGF in the amino terminal two-thirds of the gene with the exception of the sequence QEEK which was altered from the natural human sequence QEDK. The carboxy terminus was derived from the amino acid sequence of VGF and terminated with the sequence YQR TMR upstream of the natural sequence PNT. Plasmid pLEBam was digested with BssHII and BamHI. BssHII-BamHI pLE-Bam was then ligated to oligonucleotides TGF101, 102, 103, and 104, and VGF1, 2, 3, and 4 using DNA ligase and the resulting plasmids used to transform competent HB101. The transformants were selected on ampicillin and screened by restriction analysis using EcoRI, NcoI and BamHI and by nucleotide sequencing using the Maxam-Gilbert protocol. A correct construction was isolated and denoted pLEBam/TTV.

(1) Preparation of a 4.3 kb KpnI-SphI Fragment of pLEBam/TTV

Plasmid pLEBam/TTV was digested with KpnI and SphI and the 4.3 kb KpnI-SphI fragment was gel purified. This digestion removes the middle TGF domain from the synthetic gene TTV in the cloning plasmid pLEBam.

(2) Ligation and Isolation of pLEBam/TVV

Oligonucleotides VGF101 a and 102 a were ligated to the 4.3 kb KpnI-SphI fragment of pLEBam/TTV using DNA ligase and the resulting mixture was used to transform competent HB101. The transformants were selected on ampicillin and were screened by nucleotide sequencing using the Sanger-dideoxy method. A correct construct was isolated and denoted pLEBam/TVV.

```
  TGF →
 NcoI
CCATGGTTGTTTCTCACTTTAACGACTGCCCGGACTCTCATACTCAGTTTTGCTT
  M   V   V   S   H   F   N   D   C   P   D   S   H   T   Q   F   C   F

                                      VGF →
  KpnI                                 SphI
TCATGGTACCTGCCGTTTTCTGGTTCAGGAAGAAAAACCGGCATGCGTTTGCTCT
 H   G   T   C   R   F   L   V   Q   E   E   K   P   A   C   V   C   S

                EcoRI
CATGGCTACACTGGAATTCGTTGCCAGCATGTTGTTCTGGTCGACTACCAGCGT
H   G   Y   T   G   I   R   C   Q   H   V   V   L   V   D   Y   Q   R

   BamHI
TAAGGATCC
Ter
```

b. Preparation of Plasmid pLEBam/TVV

The synthetic chimeric growth factor, denoted TVV or (TGF/VGF/VGF) was assembled in the cloning vector pLE-Bam. This hybrid growth factor contained the amino acid sequence of human TGF in the N-terminal domain of the gene. The middle and C-terminal domains are derived from the truncated VGF sequence and end with the sequenceYQR upstream of the natural sequence PNT. In addition, the synthetic gene has the modification, GYACVC for GMY-CRC.

```
    TGF →
 NcoI
CCATGGTTGTTTCTCACTTTAACGACTGCCCGGACTCTCATACTCAGTTTTGCTT
  M   V   V   S   H   F   N   D   C   P   D   S   H   T   Q   F   C   F

        VGF →
   KpnI                                     SphI
TCATGGTACCTGCATCCATGCACGTGACATCGACGGCTACGCATGCGTTTGCTCT
 H   G   T   C   I   H   A   R   D   I   D   G   Y   A   C   V   C   S

                EcoRI
CATGGCTACACTGGAATTCGTTGCCAGCATGTTGTTCTGCTCGACTACCAGCGT
H   G   Y   T   G   I   R   C   Q   H   V   V   L   V   D   Y   Q   R

   BamHI
TAAGGATCC
Ter
```

B. Synthetic Platelet Factor 4 Gene

A synthetic platelet factor 4 gene was designed which uses bacterial codons optimized for high levels of expression. Single-stranded overlapping sequences were prepared, combined in an annealing medium and ligated to provide the complete gene with appropriate termini for insertion into an expression vector in reading phase to prepare a fused protein from which platelet factor 4 could be isolated. The resulting expression vector was called pHCPF4. The single-stranded segments were 5'-phosphorylated with T4 polynucleotide ligase and annealed by combining 200 pM of each segment in a 30 μl reaction volume (30 mM ATP, 10 mM DTT, 10 mM $MgCl_2$ 1 μg/ml spermidine, 100 mM Tris-HCl, pH 7.8 and T4 DNA ligase. The dsDNA was digested with BssHII and BamHI and purified on a 7% native polyacrylamide gel.

The following sequence was prepared:

```
   3' GGTACCTTCGACTTCTTCTGCCTCTAGACGTCACG
5'CGCGCCATGGAAGGCTAAGAAGACGGAGATCTGCAGTGC
        M  E  A  E  E  D  G  D  L  Q  C
   |
  NH2

3'GACACGCATTTTTGATGAAGAGTCCATTCCGGAGCAGTG
5'CTGTGCGTAAAAACTACTTCTCAGGTAAGGCCTCGTCAC
   L  C  V  K  T  T  S  Q  V  R  P  R  H

3'TAGTGTAGTGAGCTCCATTAGTTTCGGCCGGGCGTCACGGGC
5'GGCATCACATCACTCGAGGTAATCAAAGCCGGCCCGCACCCG
   I  T  S  L  E  V  U  K  A  G  P  H  C  P

3'TGACGAGTCGACTAGCGCTGAGACTTTTTGCCAGCATTC
5'ACTGCTCAGCTGATCGCGACTCTGAAAAACGGTCGTAAG
   T  A  Q  L  I  A  T  L  K  N  G  R  K

3'TAGACAGATCTGGACGTCCGAGGCGACATGTTTTTTTAG
5'ATCTGTCTAGACCTGCAGGCTCCGCTGTACAAAAAAATC
  I  C  L  D  L  Q  A  P  L  Y  L  L  I

3'TAGTTTTTTGACGACCTTAGAATTCCTAG
5'ATCAAAAAACTGCTGGAATCTTAAG
   I  K  K  L  L  E  S  ***
                      |
                     COOH
```

C. DNA Cloning of Oncostatin M

1. Preparation of cDNA Libraries

Poly(A)$^+$ RNA obtained from U937 cells treated with media containing phorbol 12-myristate 13-acetate PMA (10 ng/ml) for 16, 36, and 52 hours was pooled and used for cDNA synthesis and cloning into a λgt 10 vector, essentially as described by Huynh et al., *DNA Cloning Techniques: A Practical Approach*, D. Glover (ed) (1984). Briefly, 10 μg poly(A$^+$) RNA was reverse transcribed in the presence of 50 pmol oligo dT. The second strand was synthesized using DNA polymerase I and the cDNA was treated with Sl nuclease to eliminate the hair pin loop. The cDNA was then dG tailed by treatment with terminal deoxy nucleotidyl transferase. The dG tailed cDNA was subsequently chromatographed on Biogel A-50 column to eliminate cDNA smaller than 300 bp. The sized dG tailed cDNA were ligated into EcoRI cut λgt 10 in the presence of single stranded 16 nucleotide-long linker molecule comprising, from the 5' end, AATT followed by 12 deoxycytosine residues (Webb et al., 1987). The ligated DNA was packaged in vitro (Grosveld et al., *Gene* (1981) 13:227–237) and the phage was used to infect *E. coli* C60 Hfl$^+$. This technique gave $3\times10^6$ recombinants/μg cDNA. Nitrocellulose filter plaque lifts were done in duplicate and the filters were probed using long, best guess 35 to 50 nucleotide long probes. The oligonucleotide probes were derived from the peptide sequences obtained by automated repetitive Edman degradation. The purified Oncostatin M sequence was either derived from the N-terminal of the protein or by sequencing the protease-generated lysine peptides.

Initial screening of the λgt 10 library was done using a 50 mer oligonucleotide probe. The probe was derived from the lysine peptide.

```
Peptide 1:
   (K)  A   Q   D   L   E   R   S   G   L   N   I   E
3'  TTC CGG GTC CTG GAC CTC GCC AGA CCG GAC TTG TAA CTC

 D   L   E   K
CTG GAC CTC TT 5'
```

λgt 10 clones showing positive reactivity to [$^{32}$P]-labeled above oligonucleotide were plaque purified. Eight clones were obtained. Southern blot analysis showed that the positively reacting cDNA inserts in the clones ranged between 600 bp to 2 Kb. Subsequently, Southern blots were done using a 35 mer oligonucleotide (encoding amino acids 53–64) and a 41 mer oligonucleotide (encoding amino acids 22–35). Only one clone showed positive reactivity with all three radiolabeled oligonucleotide probes.

The cDNA insert of the λgt 10 clone (λ0M) was found to be approximately 2.1 Kb. The cDNA insert flanked by EcoRI sites at 5' and 3' ends was subcloned in the EcoRI site of the polylinker region of the plasmid vector pEMBL18 (Dente et al., *Nucleic Acid Res.* (1983) 11:1645–1655. The recombinant was termed pOncM46. Subsequently, additional cDNA clones were obtained by specific priming using oligonucleotides derived from the 5' coding region of the Oncostatin M gene and a genomic clone containing the entire gene was isolated.

2. Restriction Site Mapping

A restriction map of the clone pOncM46 coding Oncostatin M protein was obtained by standard single or double digestions of the plasmid DNA. The coding region has four PstI sites, a BglII site and a SmaI site.

3. DNA Sequence of Oncostatin M

The entire nucleotide sequence of the cDNA clones was obtained and a consensus sequence was determined as follows:

```
CGGGCCGGAGCACGGGCACCCAGCATGGGGGTACTGCTCACACAGAGGAC
                          M  G  V  L  L  T  Q  R  T

GCTGCTCAGTCTGGTCCTTGCACTCCTGTTTCCAAGCATGGCGAGCATGG
 K  K  S  K  V  K  A  K  K  F  O  S  N  A  S  M  A

CGGCTATAGGCAGCTGCTCGAAAGAGTACCGCGTGCTCCTTGGCCAGCTC
  A  I  G  S  C  S  K  E  Y  R  V  L  L  G  Q  L

CAGAAGCAGACAGATCTCATGCAGGACACCAGCAGACTGCTGGACCCCTA
Q  K  Q  T  D  L  M  Q  D  T  S  R  L  L  D  P  Y

TATACGTATCCAAGGCCTGGATGTTCCTAAACTGAGAGAGCACTGCAGGG
 I  R  I  Q  G  L  D  V  P  K  L  R  E  H  C  R  E

AGCGCCCCGGGGCCTTCCCCAGTGAGGAGACCCTGAGGGGGCTGGGCAGG
  R  P  G  A  F  P  S  E  E  T  L  R  G  L  G  R

CGGGGCTTCCTGCAGACCCTCAATGCCACACTGGGCTGCGTCCTGCACAG
R  G  F  L  Q  T  L  N  A  T  L  G  C  V  L  H  R

ACTGGCCGACTTAGAGCAGCGCCTCCCCAAGGCCCAGGATTTGGAGAGGT
 L  A  D  L  E  Q  R  L  P  K  A  Q  D  L  E  R  S

CTGGGCTGAACATCGAGGACTTGGAGAAGCTGCAGATGGCGAGGCCGAAC
  G  L  N  I  E  D  L  E  K  L  Q  M  A  R  P  N

ATCCTCGGGCTCAGGAACAACATCTACTGCATGGCCCAGCTGCTGGACAA
I  L  G  L  R  N  N  I  Y  C  M  A  Q  L  L  D  N
```

-continued

```
CTCAGACACGGCTGAGCCCACGAAGGCTGGCCGGGGGGCCTCTCAGCCGC
 S  D  T  A  E  P  T  K  A  G  R  G  A  S  Q  P  P

CCACCCCCACCCCTGCCTCGGATGCTTTTCAGCGCAAGCTGGAGGGCTGC
  T  P  T  P  A  S  D  A  F  Q  R  K  L  E  G  C

AGGTTCCTGCATGGCTACCATCGCTTCATGCACTCAGTGGGGCGGGTCTT
R  F  L  H  G  Y  H  R  F  M  H  S  V  G  R  V  F

CAGCAAGTGGGGGGAGAGCCCGAACCGGAGCCGGAGACACAGCCCCCACC
 S  K  W  G  E  S  P  N  R  S  R  R  H  S  P  H  Q

AGGCCCTGAGGAAGGGGGTGCGCAGGACCAGACCCTCCAGGAAAGGCAAG
  A  L  R  K  G  V  R  R  T  R  P  S  R  K  G  K

AGACTCATGACCAGGGGACAGCTGCCCCGGTAGCCTCGAGAGCACCCCTT
R  L  M  T  R  G  Q  L  P  R

GCCGGTGAAGGATGCGGCAGGTGCTCTGTGGATGAGAGGA

*

ACCATCGCAGGATGACAGCTCCCGGGTCCCCAAACCTGTTCCCCTCTGCT

ACTAGCCACTGAGAAGTGCACTTTAAGAGGTGGGAGCTGGGCAGACCCCT

CTACCTCCTCCAGGCTGGGAGACAGAGTCAGGCTGTTGCGCTCCCACCTC

AGCCCCAAGTTCCCCAGGCCCAGTGGGGTGGCCGGGCGGGCCACGCGGGA

CCGACTTTCCATTGATTCAGGGGTCTGATGACACAGGCTGACTCATGGCC

GGGCTGACTGCCCCCCTGCCTTGCTCCCCGAGGCCTGCCGGTCCTTCCCT

CTCATTGACTTGCAGGGCCGTTGCCCCCAGACTTCCTCCTTTCCGTGTTT

CTGAAGGGGAGGTCACAGCCTGAGCTGGCCTCCTATGCCTCATCATGTCC

CAAACCAGACACCTGGATGTCTGGGTGACCTCACTTTAGGCAGCTGTAAC

AGCGGCAGGGTGTCCCAGGAGCCCTGATCCGGGGGTCCAGGGAATGGAGC

TCAGGTCCCAGGCCAGCCCCGAAGTCGCCACGTGGCCTGGGGCAGGTCAC

TTTACCTCTGTGGACCTGTTTTCTCTTTGTGAAGCTAGGGAGTTAGAGGC

TGTACAAGGCCCCCACTGCCTGTCGGTTGCTTGGATTCCCTGACGTAAGG

TGGATATTAAAAATCTGTAAATCAGGACAGGTGGTGCAAATGGCGCTGGG

AGGTGTACACGGAGGTCTCTGTAAAAGCAGACCCACCTCCCAGCGCCGGG

AAGCCCGTCTTGGGTCCTCGCTGCTGGCTGCTCCCCCTGGTGGTGGATCC

TGGAATTTTCTCACGCAGGAGCCATTGCTCTCCTAGAGGGGGTCTCAGAA

ACTGCGAGCCCAGTTCCTTGGAGGGACATGACTAATTTATCGATTTTTAT

CAATTTTTATCAGTTTTATATTTATAAGCCTTATTTATGATGTATATTTA

ATGTTAATATTGTGCAAACTTATATTTAAAACTTGCCTGGTTTCTAAA
```

The consensus sequence was further verified by comparison with the sequence of the genomic clone. The open reading frame continues from nucleotide 1 to the stop codon at nucleotide 783. The open reading frame codes for 8 amino acids upstream from the putative initiating methionine. The nucleotide sequence coding for the putative initiating methionine agrees with the consensus sequence for the initiating methionine (Kozak, *Cell* (1986) 44:283–292).

The amino acid sequence of the Oncostatin M polypeptide deduced from the consensus cDNA sequence shows that Oncostatin M is derived from a 253 amino acid precursor polypeptide. The amino terminal sequence of purified Oncostatin M (see above and and Zarling, et al., *Proc. Natl. Acad. Sci. USA* (1986) 83:9739–9743) occurs at amino acid 26. It is preceded by a hydrophobic region that appears to function as a signal sequence. The mature protein has 228 amino acids with a molecular weight of 26,000 which is in close agreement with the approximate $M_r$=28,000 as determined by the polyacrylamide gel electrophoresis of the purified Oncostatin M (Zarling, et al., 1986 supra).

Earlier protein chemistry work (Zarling et al., 1986 supra) showed that Oncostatin M is a glyco-protein. The cDNA clone sequence suggests two potential N-glycosylation sites (Hubbard and Ivatt, *Ann. Rev. Biochem.* (1981) 50:555–583) located at amino acids 76 and 193 of the mature protein. The nucleotide-derived protein sequence shows that Oncostatin M is an extremely hydrophilic molecule. Twenty four base pairs of the 5' untranslated region and 1054 base pairs of 3' untranslated regions were obtained in the different cDNA clones. However, a polyA tail and polyadenylation recognition site were not obtained.

4. Preparation of pOncMVV2

The 2.1 kb Oncostatin M cDNA was excised from the λ phage recombinant, pOncM46, by EcoRI digestion. The insert was cloned into pEMBL18 (Dente et al., *Nucl. Acid Res.* (1983) 11:1645–1655) at the EcoRI site to produce clone pOncM46-15 vector with the Oncostatin M coding sequence opposed to the β-gal sequence. The 5' noncoding sequence of Oncostatin M was removed by SalI and BglII double digestion of pOncM46-15 and replaced by a synthetic 80 bp SalI-BglII fragment to provide new BamHI and NcoI sites. The resulting clone was termed pOncMEV5. The sequence of the 80 bp fragment is as follows:

5'-TCGACGGATCCACCATGGCGGCGATCGGCAGCTGCTCG

3'-GCCTAGGTGGTACCGCCGCTAGCCGTCGACGAGC

AAAGAGTACCGCGTGCTCCTTGGC-
CAGCTCCAGAAGCAGACA-3'

TTTCTCATGGCGCACGAGGAACCGGTC-
GAGGTCTTCGTCTGTCTAG-5

The coding sequence of Oncostatin M was excised from pOncMEV5 by XhoI and SalI double digestion as a 0.7 kb fragment and cloned into the pUC8 vector as the SalI site. The clone pOncMVV2, containing the cDNA insert with the coding sequence opposed to the lacZ' sequence, was isolated. The 0.7 kb NcoI-BamHI and the 0.7 kb BamHI-BamHI fragment excised from clone pONcMVV2 were used to construct a λpL-based (pBM16/NDP/OncM) expression vector.

EXAMPLE IV

Expression of the Polypeptide of Interest as a Fusion Protein with the N-Protein A. Modified Synthetic TGF 1. Preparation of pBM11/N/TGF The modified human TGF was expressed in this system as part of a fusion with the 33 N-terminal amino acids of the N-gene and has the sequence QEEK replacing the human sequence QEDK.

a. Preparation of a 780 bp SphI-PvuI fragment of pBM11/N/TTV

Plasmid pBM11/N/TTV was digested with SphI and PvuI and the 780 bp SphI-PvuI fragment was gel purified. This fragment contains part of the pBM11 plasmid at the PvuI end and at the SPhI end, the N-gene and N-terminal two-thirds of the human TGF gene.

b. Preparation of the 5 kb BamHI-PvuI fragment of pBM11/N/TTV

Plasmid pBM11/N/TTV was digested with BamHI and PvuI and the 5 kb BamHI-PvuI fragment was gel purified.

c. Ligation and isolation of pBM11/N/TGF:

Oligonucleotides TGF 205 and 206, the 780 bp SphI-PvuI fragment and the 5 kb BamHI-PvuI fragment of pBM11/N/

TTV were ligated together and used to transform competent HB101. The transformants were selected on neomycin and were screened by restriction analysis using EcoRI and nucleotide sequencing following the Sanger-dideoxy method. A correct construction was isolated and denoted pBM11/N/TGF.

```
N-gene →
ATGGATGCACAAACACGCCGCCGCGAACGTCGCGCAGAGAAACAGGCTCAATGGA
M  D  A  Q  T  R  R  R  E  R  R  A  E  K  Q  A  Q  W  K

                                                BamHI
AAGCAGCAAATCCCCTGTTGGTTGGGGTAAGCGCAAAACCAGTTCGGATCCGCAT
  A  A  N  P  L  L  V  G  V  S  A  K  P  V  R  I  R  M

 TGF →
GGTTGTTTCTCACTTTAACGACTGCCCGGACTCTCATACTCAGTTTTGCTTTCAT
 V  V  S  H  F  N  D  C  P  D  S  H  T  Q  F  C  F  H

 KpnI                                     SphI
GGTACCTGCCGTTTTCTGGTTCAGGAAGAAAAACCGGCATGCGTTTGCCATTCTG
G  T  C  R  F  L  V  Q  E  E  K  P  A  C  V  C  H  S  G

                                               BamHI
GCTAGGTTGGCGCACGTTGCGAACACGCTGACCTGCTGGCTTAAGGATCC
  Y  V  G  A  R  C  E  H  A  D  L  L  A  Ter
```

B. Modified Synthetic TGF-VGF Hybrid

1. Preparation of pBM11/N/TTV

In this construct, a synthetic modified TTV chimeric gene was expressed as the C-terminal portion of a fusion protein having the first 33 amino acids of the N-gene at the N-terminus. This hybrid growth factor contained the amino acid sequence of human TGF in the amino terminal two-thirds of the gene with the exception of the sequence QEEK which was altered from the natural human sequence QEDK. The carboxy terminus was derived from the amino acid sequence of VGF and terminated with the sequence YQR upstream of the natural sequence PNT.

a. Preparation of NcoI(blunt)-BamHI TTV synthetic gene

Plasmid pLEBam/TTV was digested with NcoI and the ends were made blunt by filling in the overhangs using the Klenow fragment of DNA polymerase. The DNA was then digested with BamHI and the 170 bp NcoI(blunt)-BamHI TTV fragment was gel purified.

b. Preparation of BamHI digested pBM11

Plasmid pBM11 was digested with BamHI.

c. Ligation and isolation of pBM11/N/TTV BamHI digested pBM11, the NcoI(blunt)-BamHI TTV fragment, and BamHI linkers (5'GATCCG3') were ligated together using DNA ligase and the resulting mixture was used to transform competent HB101. The transformants were selected on neomycin and were screened using restriction analysis and nucleotide sequencing using the Sanger-dideoxy method. A correct construct was isolated and denoted pBM11/N/TTV.

```
N-gene →
ATGGATGCACAAACACGCCGCCGCGAACGTCGCGCAGAGAAACAGGCTCAATGGA
M  D  A  Q  T  R  R  R  E  R  R  A  E  K  Q  A  Q  W  K

                                                BamHI
AAGCAGCAAATCCCCTGTTGGTTGGGGTAAGCGCAAAACCAGTTCGGATCCGCAT
  A  A  N  P  L  L  V  G  V  S  A  K  P  V  R  I  R  M

 TGF →
GGTTGTTTCTCACTTTAACGACTGCCCGGACTCTCATACTCAGTTTTGCTTTCAT
 V  V  S  H  F  N  D  C  P  D  S  H  T  Q  F  C  F  H

    KpnI                                 SphI    VGF →
GGTACCTGCCGTTTTCTGGTTCAGGAAGAAAAACCGGCATGCGTTTGCCATTCTG
G  T  C  R  F  L  V  Q  E  E  K  P  A  C  V  C  H  S  G

          EcoRI
GCTACACTGGAATTCGTTGCCAGCATGTTGTTCTGGTCGACTACCAGCGTTAAG
  Y  T  G  I  R  C  Q  H  V  V  L  V  D  Y  Q  R  Ter

BamHI
CATCC
```

C. Synthetic Platelet Factor 4

1. Preparation of pBM11/N/PF4 (N-gene/Platelet Factor 4)

This plasmid was prepared as described above for pBM11/N/TTV, except that the synthetic PF4 gene was used in place of the chimeric TTV gene. The nucleotide sequence and corresponding amino acid sequence of the synthetic platelet factor 4 gene in fusion downstream of the nucleotide sequences coding for the first 33 amino acids of the bacteriophage λ N-gene in the expression vector pBM11 is as follows.

```
N-gene ->
 M   D   A   Q   T   R   R   R   E   R   R   A   E   K
ATG GAT GCA CAA ACA CGC CGC CGC GAA CGT CGC GCA GAG AAA

 Q   A   Q   W   K   A   A   N   P   L   L   V   G   V
CAG GCT CAA TGG AAA GCA GCA AAT CCC CTG TTG GTT GGG GTA

                                    PF4 ->
 S   A   K   P   V   R   I   R   M   E   A   E   E   D
AGC GCA AAA CCA GTT CGG ATC CGC ATG GAA GCT GAA GAG GAT

 G   D   L   Q   C   L   C   V   K   T   T   S   Q   V
GGA GAT CTG CAA TGC CTG TGC GTT AAG ACT ACG TCT CAG GTT

 R   P   R   H   I   T   S   L   E   V   I   K   A   G
AGA CCG CGG CAT ATC ACT AGC CTC GAG GTT ATC AAA GCG GGC

 P   H   C   P   T   A   Q   L   I   A   T   L   K   N
CCA CAC TGT CCG ACT GCG CAG CTG ATC GCG ACT CTG AAA AAC

 G   R   K   I   C   L   D   L   Q   A   P   L   Y   K
GGC CGT AAA ATA TGT CTG GAT CTG CAG GCA CCG CTG TAC AAG

 K   I   I   K   K   L   L   E   S  ***
AAA ATC ATC AAA AAG CTT CTC GAG TCT TGA
```

EXAMPLE V

Preparation of the Polypeptide of Interest as a Fusion Protein with the N-Protein and a Cleavage Site A. Modified Synthetic VGF 1. Preparation of pBM11/NDP/VGFA The N-terminal sequence of the synthetic VGFA gene is a truncated version of the natural VGF sequence and begins with the sequence DIPAIR. In this plasmid the VGFA fragment is located downstream of 32 amino acids of the lambda N-protein and the dipeptide aspartic acid-proline In order to preserve the KpnI cloning site, the synthetic sequence was altered to code for CLHCGTC instead of the natural VGF sequence CLHGDC and terminates with the sequence YQR upstream of the natural sequence PNT. In addition, the VGFA gene codes for the sequence GYACVC which replaces the natural sequence GMYCRC.

a. Preparation of a KpnI-BamHI 80 bp C-terminal fragment of the synthetic VGF gene Plasmid pLEBam/TVVi was digested with KpnI and BamHI and the 80 bp KpnI-BamHI fragment was gel purified. This fragment contains the C-terminal two-thirds of the synthetic VGF gene with the KpnI site at the 5' end.

b. Preparation of BamHI digested dephosphorylated pBM11

Plasmid pBM11/N/TTV was digested with BamHI and the 5' phosphates were removed by treatment with calf intestinal alkaline phosphatase. The 5.6 kp BamHI plasmid fragment was gel purified.

c. Ligation and isolation of pBM11/NDP/VGFA Oligonucleotides VGF 103a, 104a, the 5.6 kb BamHI fragment of pBM11 and the 80 bp KpnI-BamHI fragment of pLEBam/TVV were ligated together using DNA ligase and then used to transform competent HB101. The transformants were selected on neomycin and were screened by restriction analysis using ClaI and nucleotide sequencing following the Sanger-dideoxy technique. A correct construction was isolated and denoted pBM11/NDP/VGFA. This construction has the sequences GTC and GYACVC instead of the authentic VGF sequences GDC and GMYCRC.

```
N-gene →
ATGGATGCACAAACACGCCGCCGCGAACGTCGCGCAGAGAAACAGGCTCAATGGA
M  D  A  Q  T  R  R  R  E  R  R  A  E  K  Q  A  Q  W  K

                                                   ****
                                                   ClaI
AAGCAGCAAATCCCCTGTTGGTTGGGGTAAGCGCAAAACCAGTTCGGATCGATC
  A  A  N  P  L  L  V  G  V  S  A  K  P  V  R  I  D  P

NcoI VGF →
CCATGGACATCCCGGCTATCCGTCTGTGCGGCCCGGAAGGCGACGGCTACTGCCT
  M  D  I  P  A  I  R  L  C  G  P  E  G  D  G  Y  C  L

  KpnI                                   SphI
GCATGGTACCTGCATCCATGCACGTGACATCGACGCTGACGCATGCGTTTGCTCT
 H  G  T  C  I  H  A  R  D  I  D  G  Y  A  C  V  C  S

                EcoRI
CATGGCTACACTGGAATTCGTTGCCAGCATGTTGTTCTGGTCGACTACCAGCGT
H  G  Y  T  G  I  R  C  Q  H  V  V  L  V  D  Y  Q  R

  BamHI
TAAGGATCC
Ter
```

2. Preparation of pBM11/NDP/VGFa

The N-terminal sequence of VGFa is a truncated version of the natural VGF sequence and starts with the sequence DIPAIR. In addition, the VGFa sequence contains the altered sequences GTC and GYACRC instead of the natural VGF sequences GDC and GMYCRC. In this plasmid the VGFa gene is located downstream of 32 amino acids of the lambda N-protein and the dipeptide aspartic acid-proline. Treatment of the purified fusion protein with formic acid results in cleavage at the acid labile aspartic acid-proline peptide bond allowing separation of the VGFa protein from the lambda N-protein amino-terminus. Cleavage is such that the VGFa protein is left with the proline residue at the amino terminus.

a. Preparation of SphI digested, dephosphorylated pBM11/DP/VGFA Plasmid pBM11/DP/VGFA (10 μg) was digested with 30 units of SphI and the 5' phosphates were removed by treatment with calf intestinal alkaline phosphatase. The 5 kb plasmid fragment was recovered after electrophoresis on an agarose gel.

b. Preparation of an EcoRI-SphI 70 bp fragment of pBM11/DP/VGFA

Plasmid pBM11/DP/VGFA (10 μg) was digested with 30 units of EcoRI and then 30 units of SphI. The 70 bp fragment was recovered after electrophoresis on an agarose gel.

3. Ligation and Isolation of pBM11/NDP/VGFa

The 24 bp fragment containing oligonucleotides VGF 1A and 2A, the 5 kb SphI fragment and the 70 bp EcoRI-SphI fragment of pBM11/DP/VGFA were ligated together and the mixture was used to transform competent *E. coli* HB101 cells. The transformants were screened by nucleotide sequencing using the Sanger-dideoxy nucleotide method. A correct clone was isolated and denoted pBM11/NDP/VGFa.

factor contains the amino acid sequence of human TGF in the amino terminal two-thirds of the gene with the exception of the sequence QEEK which was altered from the natural human TMR sequence QEDK. The carboxy terminus was derived from the amino acid sequence of VGF and terminated with the sequence YQR upstream of the natural sequence PNT.

a. Preparation of 5 kb NcoI pBM11 plasmid fragment

Plasmid pBM11/NDP/VGFA was digested with NcoI and the 5 kb NcoI plasmid fragment was gel purified. This fragment has one NcoI overhang at the aspartic acid-proline cleavage site downstream of the sequences coding for the first 32 amino acids of the N-gene. The other NcoI site is in the neomycin resistance gene.

b. Preparation of 0.6 kb NcoI-BamHI pBM11 plasmid fragment

Plasmid pBM11/N/TTV was digested with NcoI and BamHI and the 0.6 kb NcoI-BamHI plasmid fragment was gel purified. This fragment has the NcoI overhang in the neomycin resistance gene.

c. Preparation of the 170 bp synthetic TGF/TGF/VGF fragment

Plasmid pLEBam/TTV was digested with NcoI and BamHI and the NcoI-BamHI 170 bp fragment containing the TGF/TGF/VGF synthetic gene was gel purified. This fragment has the NcoI overhang at the 5' end of the gene and the BamHI overhang at the 3' end of the gene.

d. Ligation and isolation of pBM11/NDP/TTV

The 5 kb NcoI and the 0.6 kb NcoI-BamHI plasmid fragments were ligated with the 170 bp NcoI-BamHI TTV gene using DNA ligase and the resulting mixture was used

```
N-gene →
ATGGATGCACAAACACGCCGCCGCGAACGTCGCGCAGAGAAACAGGCTCAATGGA
M  D  A  Q  T  R  R  R  E  R  R  A  E  K  Q  A  Q  W  K

                                                    ****
                                                   ClaI
AAGCAGCAAATCCCCTGTTGGTTGGGGTAAGCGCAAAACCAGTTCGGATCGATC
  A  A  N  P  L  L  V  G  V  S  A  K  P  V  R  I  D  P

NcoI VGF →
CCATGGACATCCCGGCTATCCGTCTGTGCGGCCCGGAAGGCGACGGCTACTGCCT
  M  D  I  P  A  I  R  L  C  G  P  E  G  D  G  Y  C  L

    KpnI                                      SphI
GCATGGTACCTGCATCCATGCACGTGACATCGACGCTGACGCATGCGTTTGCTCT
 H  G  T  C  I  H  A  R  D  I  D  G  Y  A  C  V  C  S

              EcoRI
CATGGCTACACTGGAATTCGTTGCCAGCATGTTGTTCTGGTCGACTACCAGCGT
H  G  Y  T  G  I  R  C  Q  H  V  V  L  V  D  Y  Q  R

    BamHI
TAAGGATCC
Ter
```

B. Modified Synthetic TGF-VGF Hybrids

1. Preparation of pBM11/NDP/TTV

In this construct, the synthetic modified TTV chimeric gene is expressed as the C-terminal portion of a fusion protein having the first 32 amino acids of the N-gene at the N-terminus. An acid labile aspartic acid-proline dipeptide separates the two parts of the fusion. The hybrid growth to transform competent HB101. The transformants were selected on neomycin such that only colonies with correctly reconstructed neomycin resistance genes would survive. Transformants were screened using restriction analysis with NcoI and nucleotide sequencing using the Sanger-dideoxy technique. A correct construction was isolated and denoted pBM11/NDP/TTV.

```
N-gene →
ATGGATGCACAAACACGCCGCCGCGAACGTCGCGCAGAGAAACAGGCTCAATGGA
M  D  A  Q  T  R  R  R  E  R  R  A  E  K  Q  A  Q  W  K

                                                   ClaI
AAGCAGCAAATCCCCTGTTGGTTGGGGTAAGCGCAAAACCAGTTCGGATCGATC
 A  A  N  P  L  L  V  G  V  S  A  K  P  V  R  I  D  P

NcoI TGF →
CCATGGTTGTTTCTCACTTTAACGACTGCCCGGACTCTCATACTCAGTTTTGCTT
 M  V  V  S  H  F  N  D  C  P  D  S  H  T  Q  F  C  F

    KpnI                         SphI    VGF →
TCATGGTACCTGCCGTTTTCTGGTTCAGGAAGAAAAACCGGCATGCGTTTGCTCT
 H  G  T  C  R  F  L  V  Q  E  E  K  P  A  C  V  C  S

                EcoRI
CATGGCTACACTGGAATTCGTTGCCAGCATGTTGTTCTGGTCGACTACCAGCGT
H  G  Y  T  G  I  R  C  Q  H  V  V  L  V  D  Y  Q  R

   BamHI
TAAGGATCC
Ter
```

2. Preparation of pBM11/NDP/VTV

In this construct, the synthetic modified VTV chimeric gene was expressed as the C-terminal portion of a fusion protein having the first 32 amino acids of the N-gene at the N-terminus. An acid labile aspartic acid-proline dipeptide separates the two parts of the fusion. The hybrid growth factor contained the amino acid sequence of human TGF in the middle domain with the amino acid sequence QEEK replacing the natural sequence QEDK. The N-terminal and C-terminal domains were derived from the truncated VGF sequence and begin with the sequence DIPAIR and end with the sequence YQR which is upstream of the natural sequence PNT.

a. Preparation of a 5 kb BamHI-NcoI fragment of pBM11

Plasmid pBM11/N/TTV was digested with BamHI and NcoI and the 5 kb BamHI-NcoI fragment was gel purified. This fragment contains a BamHI overhang at the 3' end of the sequences coding for the first 32 amino acids of the N-gene and a NcoI site in the neomycin resistence gene.

b. Preparation of a 700 bp KpnI-NcoI fragment of pBM11/N/TTV

Plasmid pBM11/N/TTV was digested with KpnI and NcoI and the 700 bp KpnI-NcoI fragment was gel purified. This fragment is made up of part of plasmid pBM11 containing part of the neomycin resistence gene at the NcoI overhang, and the C-terminal VGF domain of the TTV synthetic gene at the KpnI overhang.

c. Ligation and isolation of pBM11/NDP/VTV

Oligonucleotides VGF 103a and 104a, the 5 kb BamHI-NcoI fragment of pBM11 and the 700 bp KpnI-NcoI fragment of pBM11/N/TTV were ligated together using DNA ligase and then used to transform competent HB101. The transformants were selected on neomycin and were screened by restriction analysis using ClaI and nucleotide sequencing following the Sanger-dideoxy technique.

```
N-gene →
ATGGATGCACAAACACGCCGCCGCGAACGTCGCGCAGAGAAACAGGCTCAATGGA
M  D  A  Q  T  R  R  R  E  R  R  A  E  K  Q  A  Q  W  K

                                                    ****
                                                   ClaI
AAGCAGCAAATCCCCTGTTGGTTGGGGTAAGCGCAAAACCAGTTCGGATCGATC
 A  A  N  P  L  L  V  G  V  S  A  K  P  V  R  I  D  P

NcoI VGF →
CCATGGACATCCCGGCTATCCGTCTGTGCGGCCCGGAAGGCGACGGCTACTGCCT
 M  D  I  P  A  I  R  L  C  G  P  E  G  D  G  Y  C  L

    KpnI TGF →                               SphI    VGF →
GCATGGTACCTGCCGTTTTCTGGTTCAGGAAGAAAAACCGGCATGCGTTTGCTCT
 H  G  T  C  R  F  L  V  Q  E  E  K  P  A  C  V  C  S

                EcoRI
CATGGCTACACTGGAATTCGTTGCCAGCATGTTGTTCTGGTCGACTACCAGCGT
H  G  Y  T  G  I  R  C  Q  H  V  V  L  V  D  Y  Q  R

   BamHI
TAAGGATCC
Ter
```

3. Preparation of pBM16/NDP/TVV

In this construct, the synthetic modified TVV chimeric gene was expressed as the C-terminal portion of a fusion protein having the first 32 amino acids of the N-gene at the N-terminus. An acid labile aspartic acid-proline dipeptide separates the two parts of the fusion. The hybrid growth factor contained the amino acid sequence of human TGF in the N-terminal domain. The middle and C-terminal domains were derived from the truncated VGF sequence and end with the sequence YQR. In addition, the synthetic gene has the modification GYACVC for GMYCRC.

a. Preparation of 4.3 kb NcoI-BglII fragment of pBM11/NDP/VGFa

Plasmid pBM11/NDP/VGFa was digested with NcoI and BglII and the 4.3 kb fragment was gel purified. The NcoI overhang is positioned at the aspartic acid-proline cleavage site just downstream of the first 32 amino acids of the N-gene.

b. Preparation of the 1.2 kb BamHI-BglII fragment of pBM11M5

Plasmid pBM11M5 was digested with BamHI and BglII and the 1.2 kb fragment was gel purified. This fragment differs from the normal pBM11 fragment in that the NcoI site in the neomycin resistence gene has been removed, and all subsequent vectors lacking this NcoI site are referred to as pBM16.

c. Preparation of the 170 bp NcoI-BamHI TVV synthetic gene

Plasmid pLEBam/TVV was digested with NcoI and BamHI and the 170 bp NcoI-BamHI fragment was gel purified. This synthetic gene fragment has the NcoI site at the 5'-end and the BamHI site at the 3'-end.

d. Ligation and isolation of pBM16/NDP/TVV

The 4.3 kb NcoI-BglII fragment of pBM11/NDP/VGFa and 1.2 kb BamHI-BglII fragment of pBM11M5, and the 170 bp NcoI-BamHI TVV synthetic gene fragment were ligated together using DNA ligase and the resulting mixture was used to transform competent HB101. The transformants were selected on neomycin and screened by restriction analysis and nucleotide sequencing using the Sanger-dideoxy technique. The plasmid is denoted pBM16 to indicate the loss of the NcoI restriction site in the neomycin resistance gene.

C. Synthetic EGF

1. Preparation of pBM11/NDP/EGF

In this construct the human EGF gene is expressed as part of a fusion with the 32 N-terminal amino acids of the N-gene which is downstream of an Asp-Pro cleavage site.

a. Preparation of a 5 kb NcoI fragment of pBM11

Plasmid pBM11/DP/VGFA was digested with NcoI and the 5' phosphates were removed by treatment with calf alkaline intestinal phosphatase. The 5 kb plasmid fragment was gel purified. This fragment has one NcoI overhang at the Asp-Pro cleavage site downstream of the sequences coding for the first 32 amino acids of the N-gene. The other NcoI site is in the Neomycin resistance gene.

b. Preparation of a 0.6 kb NcoI-BamHI fragment of pBM11

Plasmid pBM11/N/TTV was digested with NcoI and BamHI and the 0.6 kb NcoI-BamHI plasmid fragment was gel purified. This fragment has the NcoI overhang in the Neomycin resistance gene.

C. Ligation and Isolation of pBM11/DP/EGF

The three sets of annealed EGF oligonucleotides with an NcoI overhang at the 5' end and a BamHI overhang at the 3' end, the 5 kb NcoI fragment of pBM11 and the 0.6 kb NcoI-BamHI fragment of pBM11 were ligated together using T4 DNA Ligase and the resulting mixture was used to transform competent *E. coli* HB101. The transformants were selected on Neomycin such that only colonies with a correctly reconstructed Neomycin resistance gene would survive. The transformants were screened by restriction analysis using EcoRI and BamHI and by DNA sequencing, as described above.

```
N-gene →
ATGGATGCACAAACACGCCGCCGCGAACGTCGCGCAGAGAAACAGGCTCAATGGA
M  D  A  Q  T  R  R  R  E  R  R  A  E  K  Q  A  Q  W  K

                                                   ****
                                                   ClaI
AAGCAGCAAATCCCCTGTTGGTTGGGGTAAGCGCAAAACCAGTTCGGATCGATC
  A  A  N  P  L  L  V  G  V  S  A  K  P  V  R  I  D  P

NcoI TGF →
CCATGGTTGTTTCTCACTTTAACGACTGCCCGGACTCTCATACTCAGTTTTGCTT
  M  V  V  S  H  F  N  D  C  P  D  S  H  T  Q  F  C  F

    KpnI VGF →                          SphI
TCATGGTACCTGCATCCATGCACGTGACATCGACGGCTACGCATGCGTTTGCTCT
 H  G  T  C  I  H  A  R  D  I  D  G  Y  A  C  V  C  S

          EcoRI
CATGGCTACACTGGAATTCGTTGCCAGCATGTTGTTCTGGTCGACTACCAGCGT
H  G  Y  T  G  I  R  C  Q  H  V  V  L  V  D  Y  Q  R

   BamHI
TAAGGATCC
Ter
```

```
N-gene →
ATGGATGCACAAACACGCCGCCGCGAACGTCGCGCAGAGAAACAGCGTCAATGGA
M  D  A  Q  T  R  R  R  E  R  R  A  E  K  Q  A  Q  W  K

                                                    ***
AAGCAGCAAATCCCCTGTTGGTTGGGGTAAGCGCAAAACCAGTTCGGATCGATCC
  A  A  N  P  L  L  V  G  V  S  A  K  P  V  R  I  D  P

EGF1 → EcoRI                               EGF2 →
CATGAATTCTGACTCTGAATGCCCGCTGTCTCATGACGGCTACTGCCTGCATGAC
 M  N  S  D  S  E  C  P  L  S  H  D  G  Y  C  L  H  D

                                           EGF3 →
NsiI                                       SphI
GGCGTATGCATGTACATCGAAGCTCTGGACAAGTACGCATGCAACTGCGTTGTTG
G  V  C  M  Y  I  E  A  L  D  K  Y  A  C  N  C  V  V  G

GCTACATCGGCGAACGTTGCCAGTACCGTGACCTGAAATGGTGGGAACTGCGTTA
  Y  I  G  E  R  C  Q  Y  R  D  L  K  W  W  E  L  R  *

   BamHI
AGGATCC
```

D. Synthetic Platelet Factor 4

1. Preparation of pBM11/NDP/PF4 (N-gene/DP/Platelet Factor 4)

In this construct, the synthetic PF4 gene is expressed as the C-terminal portion of a fusion protein having the first 32 amino acids of the N-gene at the N-terminus. An acid labile aspartic acid-proline dipeptide separates the two parts of the fusion.

a. Preparation of 5 kb NcoI pBM11 plasmid fragment

Plasmid pBM11/NDP/VGFA was digested with NcoI and the 5 kb NcoI plasmid fragment was gel purified. This fragment has one NcoI overhang at the aspartic acid-proline cleavage site downstream of the sequences coding for the first 32 amino acids of the N-gene. The other NcoI site is in the neomycin resistance gene.

b. Preparation of 0.6 kb NcoI-BamHI pBM11 plasmid fragment

Plasmid pBM11/N/PF4 was digested with NcoI and BamHI and the 0.6 kb NcoI-BamHI plasmid fragment was gel purified. This fragment has the NcoI overhang in the neomycin resistance gene.

c. Ligation and Isolation of pBM11/NDP/PF4

The 5 kb NcoI and the 0.6 kb NcoI-BamHI plasmid fragments were ligated with the PF4 gene using DNA ligase and the resulting mixture was used to transform competent HB101. The transformants were selected on neomycin such that only colonies with correctly reconstructed neomycin resistance genes would survive. Transformants were screened using restriction analysis with NcoI and nucleotide sequencing using the Sanger-dideoxy technique. A correct construction was isolated and denoted pBM11/NDP/PF4.

The nucleotide sequence and corresponding amino acid sequence of the synthetic platelet factor 4 gene in fusion downstream of the nucleotide sequences coding for the first 32 amino acids of the bacteriophage λ N-gene and the acid labile dipeptide Asp-Pro (***) in the expression vector pBM11is as follows.

```
N-gene ->
 M   D   A   Q   T   R   R   R   E   R   R   A   E   K
ATG GAT GCA CAA ACA CGC CGC CGC GAA CGT CGC GCA GAG AAA

 Q   A   Q   W   K   A   A   N   P   L   L   V   G   V
CAG GCT CAA TGG AAA GCA GCA AAT CCC CTG TTG GTT GGG GTA

                            *** ***     PF4 ->
 S   A   K   P   V   R   I   D   P   M   E   A   E   E
AGC GCA AAA CCA GTT CGG ATC GAT CCC ATG GAA GCT GAA GAG

 D   G   D   L   Q   C   L   C   V   K   T   T   S   Q
GAT GGA GAT CTG CAA TGC CTG TGC GTT AAG ACT ACG TCT CAG

 V   R   P   R   H   I   T   S   L   E   V   I   K   A
GTT AGA CCG CGG CAT ATC ACT AGC CTC GAG GTT ATC AAA GCG

 G   P   H   C   P   T   A   Q   L   I   A   T   L   K
GGC CCA CAC TGT CCG ACT GCG CAG CTG ATC GCG ACT CTG AAA

 N   G   R   K   I   C   L   D   L   Q   A   P   L   Y
AAC GGC CGT AAA ATA TGT CTG GAT CTG CAG GCA CCG CTG TAC

 K   K   I   I   K   K   L   L   E   S  ***
AAG AAA ATC ATC AAA AAG CTT CTC GAG TCT TGA
```

E. Oncostatin M

1. Construction of pBM16/NDP/OncM a. Preparation of modified Oncostatin M gene fragment Plasmid pOncMVV2 containing a modified Oncostatin M gene was digested with NcoI and BamHI and the 700 bp NcoI-BamHI Oncostatin M gene was gel purified. This fragment contained the NcoI overhang at the 5' end of the gene and the BamHI overhang at the 3' end of the gene.

b. Ligation and Isolation of pBM16/NDP/OncM

The 700 bp NcoI-BamHI fragment of the modified Oncostatin M gene and the NcoI-BamHI fragment of the plasmid pBM16/NDP were ligated together with T4 ligase and transformed into competent HB101 *E. coli*. The transformants were screened for correct construction by nucleotide sequencing using the Sanger-dideoxy technique. A correct colony was chosen and termed pBM16/NDP/OncM.

c. Preparation of Oncostatin M using pBM16/NDP/OncM

*E. coli* HB101 strain harboring the plasmid pBM16/NDP/OncM, which encodes the first 32 amino acids of the bacteriophage λ N-gene fused to an acid cleavable dipeptide (DP), and the synthetic OncM gene was grown at 30° C. At an $OD_{600}$ of approximately 0.9 the temperature was raised to 42° C. which inactivates the temperature sensitive repressor inducing the PL promoter to allow transcription and translation of the NDP/OncM fusion gene. The fusion protein is characterized by having the 32 amino-terminal residues of the bacteriophage λ N-gene followed by the acid labile dipeptide Asp-Pro followed by the 228 amino acids of Oncostatin M including its N-terminal methionine.

2. Preparation of Oncostatin M Using pBMX

An 82 bp fragment was synthesized chemically as shown below.

5'-CATGGCCATTGAAGGGCGCGCTGC-
GATCGGCAGCTGCTCGAAA

3'-CGGTAACTTCCCGCGCGACGCTAGCCGTCGACGAGCTTT

GAGTACCGCGTGCTCCTTGGCCAGCTCCAGAAGCAGACA-
3'

CTCATGGCGCACGAGGAACCGGTCGAG-
GTCTTCGTCTGTCTAG-5'

The 82 bp fragment and truncated OncM cDNA (Bgl II-HindIII) isolated from pOncMVV2 were cloned into the pBM16/NDP/TVV vector prepared by NcoI and HindIII double digestion. The DNA was used to transform *E. coli* DH5α. The clone pBMX was isolated and confirmed to carry the predicted sequence. Since the coding sequence contains the -I-E-G-R-, a factor X recognition site, precisely fused to the N-terminal of mature OncM, the recombinant protein produced by pBMX should be cleaved at the R residue of -I-E-G-R- to generate mature OncM with the authentic N-terminal sequence following treatment of activated factor X. Similar procedures were used to prepare Oncostatin M using pBMX as to prepare Oncostatin M from pBM16/NDP/OncM.

EXAMPLE VI

Preparation of the Polypeptide of Interest as a Fusion Protein with the Alkaline Phosphatase Signal Sequence A. Preparation of pBM11/PAD/EGF Synthetic oligonucleotides were designed to allow insertion of DNA coding for a modified alkaline phosphatase signal peptide and a linker region with 3 cloning sites (HindIII, SmaI and BamHI) into the pBM11 expression vector downstream of the $P_L$ promoter and N gene ribosomal binding site. The nucleotide sequence was optimized to be as similar as possible to the nucleotide sequence of the amino terminus of the lambda N gene as the lambda N gene sequence has evolved with that of its ribosomal binding site for efficient ribosome initiation and translation. In addition, the second amino acid of the alkaline phosphatase signal sequence, the basic amino acid lysine was changed to an acidic amino acid, aspartic acid.

1. Preparation of 0.17 kb EcoR I-BamHI Fragment of EGF

Plasmid pBM11/NDP/EGF (30 ug) was digested with 30 units of EcoRI and then treated with 4 units of Klenow fragment of DNA polymerase to create blunt ends. The DNA was finally digested with 30 units of BamHI and the 0.17 kb fragment of the EGF gene was recovered after electrophoresis on an agarose gel. The DNA so purified has a blunted EcoRI site at the 5' end and a BamHI overhang at the 3' end.

2. Preparation of 0.5 kb Pvu I-Hind III Fragment of pBM11/PAD

Plasmid pBM11/PAD (18 ug) was digested with 30 units of HindIII and then treated with Klenow fragment to blunt the ends. The DNA was then digested with PvuI and the 0.5 kb PvuI-HindIII (blunt) fragment was recovered after electrophoresis on an agarose gel.

3. Preparation of the 5.2 kb Pvu I-BamHI Fragment of pBM11/PAD

Plasmid pBM11/PAD (18 ug) was digested with 30 units of PvuI followed by 30 units of BamHI. The 5.2 kb fragment was recovered after electrophoresis on an agarose gel.

4. Ligation and Isolation of pBM11/PAD/EGF

The 0.17 kb EcoRI (blunt)-BamHI fragment, the 0.5 kb PvuI-HindIII (blunt) fragment, and the 5.2 kb PvuI-BamHI fragment were ligated together and the resulting mixture was used to transform competent *E. coli* HB101. The transformants were screned using DNA sequencing, as described above. The desired signal sequence/EGF region had the following sequence:

```
Signal Sequence
ATGGATCAATCTACAATCGCCCTCGCACTTCTCCCACTGCTGTTCACT
M  D  Q  S  T  I  A  L  A  L  L  P  L  L  F  T

                EGF
CCAGTGACAAAAGCTAATTCTGACTCTGAATGCCCGCTGTCTCATGAC
P  V  T  K  A  N  S  D  S  E  C  P  L  S  H  D

                                 NsiI
GGCTACTGCCTGCATGACGGCGTATGCATGTACATCGAAGCTCTG
G  Y  C  L  H  D  G  V  C  M  Y  I  E  A  L

         SphI
GACAAGTACGCATGCAACTGCGTTGTTGGCTACATCGGCGAACGT
D  K  Y  A  C  N  C  V  V  G  Y  I  G  E  R

                                            BamHI
TGCCAGTACCGTGACCTGAAATGGTGGGAACTGCGTTAAGGATCC
C  Q  Y  R  D  L  K  W  W  E  L  R  *
```

The efficacy of the production of foreign protein in the pBM11/PAD expression system and the ability to purify functionally active foreign proteins from the fusion product has been show using pBM11/PAD/EGF as an example. After size exclusion chromatography (TSK-250), 10.3 mg of equivalents of active EGF fusion polypeptide was recovered from 23 g (8 liters) of *E. coli* derepressed to express the EGF gene. Forty percent of the EGF activity was derived from EDF cleaved from the signal sequence.

B. Construction of pBM11/PAD/OncM

1. Preparation of Modified Oncostatin M Gene Fragment

Plasmid pOncMVV2 containing a modified Oncostatin M gene was digested with NcoI and the 5' overhanging bases were removed by treatment with S1 nuclease leaving the fragment blunt-ended. The nuclease treatment removed the codons for the initiating methionine. The plasmid was further digested wth BamHI and the 700 bp NcoI(blunt)-BamHI Oncostatin M gene fragment was gel purified. This fragment contained the NcoI blunt end at the 5' end of the gene and BamHI overhang at the 3' end of the gene.

2. Preparation of pBM11M3/PAD Fragments

Plasmid pBM11M3/PAD containing the nucleotide sequences coding for a modified alkaline phosphatase signal sequence was digested with HindIII which cuts directly downstream of the signal sequence. The overhanging ends were filled in and made blunt using Klenow fragment of DNA polymerase. The resulting DNA was further digested with PvuI and the 680 bp HindIII(blunt)-PvuI fragment was gel purified.

Plasmid pBM11M3/PAD was also digested with BamHI and PvuI and the 5 kb BamHI-PvuI fragment was gel purified.

3. Ligation and Isolation of pBM11/PAD/OncM

The 700 bp NcoI(blunt)-BamHI Oncostatin M gene fragment, the 680 bp HindIII(blunt)-PvuI fragment of pBM11M3/PAD and the 5 kb BamHI-PvuI fragment of pBM11M3/PAD were ligated together using T4 ligase and transformed into competent HB101 *E. coli.* Correct construction was assayed by nucleotide sequencing using the Sanger-dideoxy technique. A correct colony was chosen and designated pBM11/PAD/OncM.

C. Preparation of pBM11/PAD/nVGFa

Synthetic oligonucleotides were designed to link the VGFa synthetic gene with an alkaline phosphatase modified signal sequence to provide for an optimal signal sequence cleavage site by coding for the additional N-terminal residues occurring immediately down-stream of the signal sequence cleavage site in the natural VGF, denoted extreme N-terminus above. The nVGFa sequence contains the altered sequences GTC and GYACRC instead of the natural VGF sequences GDC and GMYCRC and terminates with the sequence YQR upstream of the natural sequence PNT. In this expression system, for the majority of the molecules, the signal sequence remains attached to the nVGFa forming a fusion protein with nVGFa at the C-terminus.

1. Preparation of 0.5 kb HindIII-PvuI Digested pBM11/PAD

Plasmid pBM11/PAD was digested with HindIII and PvuI and the 0.5 kb fragment was gel purified. The HindIII site is located at the C-terminus of the modified alkaline phosphatase signal sequence.

2. Preparation of the 5.2 kb PvuI-BamHI pBM11Plasmid Fragment

Plasmid pBM11/NDP/VGFa was digested with PvuI and BamHI and the 5.2 kb plasmid fragment was gel purified.

3. Preparation of the 170 bp NcoI(blunt)-BamHI Synthetic VGFa Gene

Plasmid pBM11/NDP/VGFa was digested with NcoI and the 5' overhangs were removed by treatment with S1-nuclease. This created a blunt end at the first codon of the VGFa truncated synthetic gene. The DNA was then digested with BamHI and the 170 bp NcoI(blunt)-BamHI fragment was gel purified.

4. Ligation and Isolation of pBM11/PAD/nVGFa

Oligonucleotides VGF105 and 106, the 0.5 kb HindIII-PvuI fragment of pBM11/PAD, the 5.2 kb PvuI-BamHI pBM11fragment and the 170 bp NcoI(blunt)-BamHI synthetic VGFa gene were ligated together using DNA ligase and the resulting mixture was used to transform competent HB101. The transformants were selected on neomycin and screened by restriction analysis and nucleotide sequencing using the Sanger-dideoxy technique. A correct construct was isolated containing the modified alkaline phosphatase signal sequence in frame with the nVGFa gene.

```
Signal Sequence →
ATGGATCAATCTACAATCGCCCTCGCACTTCTCCCACTGCTGTTCACTCCAGTGA
M  D  Q  S  T  I  A  L  A  L  L  P  L  L  F  T  P  V  T

       nVGF →
CAAAAGCTGACTCTGGTAACGCTATCGAAACTACTTCTCCGGAAATCACTAACGC
  K  A  D  S  G  N  A  I  E  T  T  S  P  E  I  T  N  A

TACTACTGACATCCCGGCTATCCGTCTGTGCGGCCCGGAAGGCGACGGCTACTGC
 T  T  D  I  P  A  I  R  L  C  G  P  E  G  D  G  Y  C

       KpnI                                 SphI
CTGCATGGTACCTGCATCCATGCACGTGACATCGACGGCTACGCATGCCGTTGCT
L  H  G  T  C  I  H  A  R  D  I  D  G  Y  A  C  R  C  S

                EcoRI
CTCATGGCTACACTGGAATTCGTTGCCAGCATGTTGTTCTGGTCGACTACCAGCG
  H  G  Y  T  G  I  R  C  Q  H  V  V  L  V  D  Y  Q  R

     BamHI
TTAAGGATCC
 Ter
```

D. Preparation of pBM11/PAD/PF4 (Signal Sequence of Alkaline Phosphatase with Asp as Residue 2 Instead of Lys/Platelet Factor 4).

The nucleotide sequence and corresponding amino acid sequence of the synthetic platelet factor 4 gene in fusion downstream of the nucleotide sequences coding for a modified alkaline phosphatase signal peptide were prepared essentially as described above for pBM11/PAD/nVGFa, except that the synthetic PF4 gene was used instead of the synthetic VGFa gene in Step 3. The construct isolated is as follows. Predicted cleavage site is noted with (***).

```
Signal sequence ->
 M   D   Q   S   T   I   A   L   A   L   L   P   L   L
ATG GAT CAA TCT ACA ATC GCC CTC GCA CTT CTC CCA CTG CTG

                        *** PF4 ->
 F   T   P   V   T   K   A   E   A   E   E   D   G   D
TTC ACT CCA GTG ACA AAA GCT GAA GCT GAA GAG GAT GGA GAT

 L   Q   C   L   C   V   K   T   T   S   Q   V   R   P
CTG CAA TGC CTG TGC GTT AAG ACT ACG TCT CAG GTT AGA CCG

 R   H   I   T   S   L   E   V   I   K   A   G   P   H
CGG CAT ATC ACT AGC CTC GAG GTT ATC AAA GCG GGC CCA CAC

 C   P   T   A   Q   L   I   A   T   L   K   N   G   R
TGT CCG ACT GCG CAG CTG ATC GCG ACT CTG AAA AAC GGC CGT

 K   I   C   L   D   L   Q   A   P   L   Y   K   K   I
AAA ATA TGT CTG GAT CTG CAG GCA CCG CTG TAC AAG AAA ATC

 I   K   K   L   L   E   S  ***
ATC AAA AAG CTT CTC GAG TCT TGA
```

EXAMPLE VII

Expression of the Polypeptide of Interest as a Fusion Protein with the Alkaline Phosphatase Signal Sequence A. Preparation of pBM11/PAK/nVGFa (Alkaline Phosphatase Signal Sequence/nVGFa with Natural VGF N-terminus and Sequences GTC and GYACRC)

Plasmid pBM11/PAD/nVGF was mutagenized in vitro (Morinaga et al., *Biotechnology* (1984) 2:636–643) to alter the codons coding for the second amino acid in the signal sequence, namely to change the Asp (D) codon to that for Lys (K) the residue found in the natural sequence. This mutagenesis also introduced a PvuI site into the signal sequence.

```
Signal Sequence →
ATGGATCAATCTACAATCGCCCTCGCACTTCTCCCACTGCTGTTCACTCCAGTGACAAAA
M  D  Q  S  T  I  A  L  A  L  L  P  L  L  F  T  P  V  T  K

   nVGF →
GCTGACTCTGGTAACGCTATCGAAACTACTTCTCCGGAAATCACTAACGCTACTACT
A  D  S  G  N  A  I  E  T  T  S  P  E  I  T  N  A  T  T

                                                       KpnI
GACATCCCGGCTATCCGTCTGTGCGGCCCGGAAGGCGACGGCTACTGCCTGCATGGT
D  I  P  A  I  R  L  C  G  P  E  G  D  G  Y  C  L  H  G

                                     SphI
ACCTGCATCCATGCACGTGACATCGACGGCTACGCATGCCGTTGCTCTCATGGCTACACT
T  C  I  H  A  R  D  I  D  G  Y  A  C  R  C  S  H  G  Y  T

  EcoRI                                          BamHI
GGAATTCGTTGCCAGCATGTTGTTCTGGTCGACTACCAGCGTTAAGGATCC
G  I  R  C  Q  H  V  V  L  V  D  Y  Q  R  Ter
```

B. Preparation of pBM11/PAK/EGF

In this expression cassette the EGF gene is part of a fusion with the alkaline phosphatase signal sequence.

Plasmid pBM11/PAD/EGF was mutagenized in vitro to alter the codons coding for the second amino acid in the signal sequence, to change the Asp (D) codon to that for Lys (K) the residue found in the natural sequence. This mutagenesis also introduced a PvuI site into the signal sequence.

```
                PvuI
Signal Sequence →
ATGAAACAATCTACGATCGCCCTCGCACTTCTCCCACTGCTGTTCACTCCAGTGA
M  K  Q  S  T  I  A  L  A  L  L  P  L  L  F  T  P  V  T

           EGF →
CAAAAGCTAATTCTGACTCTGAATGCCCGCTGTCTCATGACGGCTACTGCCTGCA
  K  A  N  S  D  S  E  C  P  L  S  H  D  G  Y  C  L  H

             NsiI                                 SphI
TGACGGCGTATGCATGTACATCGAAGCTCTGGACAAGTACGCATGCAACTGCGTT
```

-continued

```
 D   G   V   C   M   Y   I   E   A   L   D   K   Y   A   C   N   C   V

GTTGGCTACATCGGCGAACGTTGCCAGTACCGTGACCTGAAATGGTGGGAACTGC
V   G   Y   I   G   E   R   C   Q   Y   R   D   L   K   W   W   E   L   R

      BamHI
GTTAAGGATCC
  *
```

C. Preparation of TacPak/EGF (Alkaline Phosphatase Signal Sequence/human EGF)

1. Preparation of Plasmid Fragments

Plasmid p135-1 was derived from plasmid pDR540 (Pharmacia) and contained the Cro gene SD and a Bgl II site downstream of the lac SD. pDR540 is an expression vector containing the trp-lac hybrid promoter. p135-1 was digested with Bgl II and BamHI and treated with bacterial alkaline phosphatase.

Plasmid pBM11/PAK/EGF was digested with PvuII and BamHI and the ~230 bp fragment coding for part of the alkaline phosphatase signal sequence and human EGF was isolated.

2. Preparation of TacPak1 and TacPak2 Oligonucleotides

Synthetic oligonucleotides TacPak1 and TacPak2 were designed with an overhang, compatible with the Bgl II site of p135-1 and a PvuII overhand, compatible with the PvuII site in the alkaline phosphatase/EGF PvuII/BamHI fragment. The oligonucleotides were synthesized on an Applied Biosystems Oligonucleotide Synthesizer.

```
                    BglII                 PvuI
                      |                     |
TacPak1     5' GATCTATGAAACAATCTACGAT 3'

TacPak2     3'     ATACTTTGTTAGATGC    5'
```

3. Ligation and Isolation of TacPak/EGF Clone

The Bgl II-BamHI digested p135-1, the 230 bp PAK/EGF fragment and oligonucleotides TacPak1 and TacPak2 were ligated using DNA ligase, transformed into competent HB101 and a correct construct was isolated by DNA sequencing.

```
(HindIII site of pDR540)
            |
        AAGCTTACTCCC

            trp-35        (16bp)        lac-10
CATCCCCCTG [TTGACA] ATTAATCATCGGCTCG (TATAATG)

      mRNA 5' lacI binding site    lacSD
TGTGG/AATTGTG AGCGGATAACAATTTCACAC {AGGA} AACAGGATCACTA

    PvuI
croSD  (11bp)BglII
{AGGA{ GGTTCAGATCT

Signal Sequence ->
ATGAAACAATCTACGATCGCCCTCGCACTTCTCCCACTGCTGTTCACTCCAGTGA
M   K   Q   S   T   I   A   L   A   L   L   P   L   L   F   T   P   V   T

EGF ->
CAAAAGCTAATTCTGACTCTGAATGCCCGCTGTCTCATGACGGCTACTGCCTGCA
  K   A   N   S   D   S   E   C   P   L   S   H   D   G   Y   C   L   H

          NsiI                                  SphI
TGACGGCGTATGCATGTACATCGAAGCTCTGGACAAGTACGCATGCAACTGCGTT
 D   G   V   C   M   Y   I   E   A   L   D   K   Y   A   C   N   C   V

GTTGGCTACATCGGCGAACGTTGCCAGTACCGTGACCTGAAATGGTGGGAACTGC
V   G   Y   I   G   E   R   C   Q   Y   R   D   L   K   W   W   E   L   R

      BamHI
GTTAAGGATCC
  *
```

EXAMPLE VIII

Expression of a Polypeptide of Interest as a Fusion Protein with the Alkaline Phosphatase Signal Sequence Using an Expression Cassette Comprising a Transcriptional Termination Region A. Preparation of pTCPt/EGF ([trp-35]16 bp[lac-10][lacSD] 11 bp[ATG]/Alkaline Phosphatase Signal/human EGF/trans. Term.-NEO)

This plasmid is designed to have the tac promoter elements and utilize the cro SD to express human EGF behind the alkaline phosphatase signal sequence. It has a pBR322 background with the Neomycin resistance gene.

1. Preparation of the 420 bp HindIII(blunt)-BamHI Fragment of TacPak/EGF

TacPak/EGF was digested with HindIII and then treated with the Klenow fragment of DNA polymerase to create blunt ends. The DNA was then digested with BamHI and the 420 bp fragment containing the tac promoter elements and the coding region for the alkaline phosphatase signal sequence and human EGF was isolated by agarose gel electrophoresis.

2. Preparation of the 2.8 kb EcoRI(blunt)-BamHI Fragment of pBM16t/NDP/VGFa pBM16t/NDP/VGFa was digested with EcoRI and then treated with Klenow to create blunt ends. The DNA was then digested with BamHI and the 2.8 kb fragment was isolated. This DNA fragment contains the pBR322 origin, the neomycin resistance gene with its NcoI site removed, and the gene32-like transcription terminator downstream of the BamHI site.

3. Ligation and Isolation of pTCPt/EGF

The 2.8 kb EcoRI(blunt)-BamHI fragment of pBM16t/NDP/VGFa was ligated to the 420 bp HindIII(blunt)-BamHI fragment of TacPak/EGF and the resulting DNA was used to transform competent JM109(lacIq). A correct construct was isolated by its resistance to neomycin and by DNA sequencing.

N-terminal extension downstream of the alkaline phosphatase signal sequence. The plasmid has a pBR322 background with the neomycin resistance gene.

1. Preparation of the 350 bp PvuI-BamHI Fragment of pBM11/PAK/nVGFa

Plasmid pBM11/PAK/nVGFa was digested with PvuI and BamHI and the 350 bp fragment was isolated by gel electrophoresis. This fragment contains most of the alkaline phosphatase signal sequence and the nVGFa gene.

2. Preparation of the 2.8 kb PvuI-BamHI Fragment of pTCPt/EGF

Plasmid pTCPt/EGF was digested with PvuI and BamHI and the 2.8 kb fragment was isolated by gel electrophoresis.

```
(HindIII site of pDR540)
            |
        AAGCTTACTCCC

            trp-35        (16bp)        lac-10
CATCCCCCTG [TTGACA] ATTAATCATCGGCTCG (TATAATG)

      mRNA 5' lacI binding site    lacSD
TGTGG/AATTGTG AGCGGATAACAATTTCACAC {AGGA} AACAGGATCACTA

              PvuI
croSD   (11bp)BglII Signal Sequence ->
{AGGA} GGTTCAGATCT  ATGAACAATCTACGATCGCCCTCGCACTTCTCC
                     M  K  Q  S  T  I  A  L  A  L  L  P

                             EGF ->
CACTGCTGTTCACTCCAGTGACAAAAGCTAATTCTGACTCTGAATGCCCGCTGTC
  L  L  F  T  P  V  T  K  A  N  S  D  S  E  C  P  L  S

                NsiI
TCATGACGGCTACTGCCTGCATGACGGCGTATGCATGTACATCGAAGCTCTGGAC
 H  D  G  Y  C  L  H  D  G  V  C  M  Y  I  E  A  L  D

       SphI
AAGTACGCATGCAACTGCGTTGTTGGCTACATCGGC
K  Y  A  C  N  C  V  V  G  Y  I  G

                                                 BamHI
GAACGTTGCCAGTACCGTGACCTGAAATGGTGGGAACTGCGTTAAGGATCCGTGA
E  R  C  Q  Y  R  D  L  K  W  W  E  L  R  *

           Trans. Term.
CTAATTGGGGACCCTAGAGGTCCCCTTTTTTATTTTAAAACGATC
```

B. Preparation of pTCPt/nVGFa ([trp-35]16 bp[lac-10][1acSD][croSD]11 bp[ATG]/Alkaline Phosphatase Signal/n-terminal VGFa with Sequence GTC and GYACRC)/trans. Term.-NEO)

This plasmid has the tac promoter elements and uses the cro SD to express the modified VGF gene with the 3. Ligation and Isolation of pTCPt/nVGFa The 2.8 kb fragment and the 350 bp fragment were ligated using DNA ligase and the DNA was used to transform competent JM109(lacIq). A correct construct was isolated using restriction analysis.

```
(HindIII site of pDR540)
            |
        AAGCTTACTCCC

            trp-35        (16bp)        lac-10
CATCCCCCTG [TTGACA] ATTAATCATCGGCTCG (TATAATG)

      mRNA 5' lacI binding site    lacSD
TGTGG/AATTGTG AGCGGATAACAATTTCACAC {AGGA} AACAGGATCACTA

              PvuI
croSD   (11bp)BglII Signal Sequence ->
{AGGA} GGTTCAGATCT  ATGAACAATCTACGATCGCCCTCGCACTTCTCC
```

-continued

```
               M   K   Q   S   T   I   A   L   A   L   L   P

     nVGF ->
ACTGCTGTTCACTCCAGTGACAAAAGCTGACTCTGGTAACGCTATCGAAACTACT
 L   L   F   T   P   V   T   K   A   D   S   G   N   A   I   E   T   T

TCTCCGGAAATCACTAACGCTACTACTGACATCCCGGCTATCCGTCTGTGCGGCC
S   P   E   I   T   N   A   T   T   D   I   P   A   I   R   L   C   G   P

                                   KpnI
CGGAAGGCGACGGCTACTGCCTGCATGGTACCTGCATCCATGCACGTGACATCGA
   E   G   D   G   Y   C   L   H   G   T   C   I   H   A   R   D   I   D

   SphI                              EcoRI
CGGCTACGCATGCCGTTGCTCTCATGGCTACACTGGAATTCGTTGCCAGCATGTT
 G   Y   A   C   R   C   S   H   G   Y   T   G   I   R   C   O   H   V

                           BamHI                 Trans.
GTTCTGGTCGACTACCAGCGTTAAGGATCCGTGACTAATTGGGGACCCTAGAGGT
 V   L   V   D   Y   Q   R   *

Term.
CCCCTTTTTTATTTTAAAACGATC
```

C. Preparation of pTNPt/EGF ([trp-35]17 bp[lac-10][nSD]8 bp[ATG]/Alkaline Phosphatase Signal/human EGF/trans. Term.-NEO)

This plasmid is designed to have the tac promoter elements and utilize the N-gene SD to express human EGF behind the alkaline phosphatase signal sequence. It has a pBR322 background with the Neomycin resistance gene.

1. Preparation of 2.8 kb PvuI-BamHI pTNPt

Plasmid pTNPt was digested with PvuI and BamHI and the 2.8 kb fragment was isolated by gel electrophoresis.

2. Preparation of 300 bp PvuI-BamHI Fragment of pBM11/PAK/EGF

Plasmid pBM11/PAK/EGF was digested with PvuI and BamHI and the 300 bp fragment was isolated.

3. Ligation and Isolation of pTNPt/EGF

The 2.8 kb fragment and the 300 bp fragment were ligated using DNA ligase and the DNA was transformed into competent JM109(LacIq). A correct construct was isolated by restriction analysis and by DNA sequencing.

```
                                    (EcoRI site of pBM11)
                                               |
                                            GAATTACTCCCCATCC

                                SstI
      trp-35       (17bp)          lac-10        5'lac
CCCTG [TTGACA] ATTAATCATCGAGCTCG (TATAATG) TGTGG/AATTG

                               BsmI
mRNA->                     n mRNA->
TGTGAGCGGATAACAATTTCACACAGCATTCAAAGCAGAAGGCTTTGGGGTGTGT

GATACGAAACGAAGCATTGGCCGTAAGTGCGATTCCGGATTAGCTGCCAATGTGC

CAATCGCGGGGGGTTTTCGTTCAGGACTACAACTGCCACACACCACCAAAGCTAA

                                              PvuI
      nSD     (8bp)  Signal Sequence ->
CTGAC {AGGA} GAATCCAG ATGAAACAATCTACGATCGCCCTCGCACTTCTC
                      M   K   Q   S   T   I   A   L   A   L   L

                                      EGF ->
CCACTGCTGTTCACTCCAGTGACAAAAGCTAATTCTGACTCTGAATGCCCGCTGT
P   L   L   F   T   P   V   T   K   A   N   S   D   S   E   C   P   L   S

                                         NsiI
CTCATGACGGCTACTGCCTGCATGACGGCGTATGCATGTACATCGAAGCTCTGGA
   H   D   G   Y   C   L   H   D   G   V   C   M   Y   I   E   A   L   D

     SphI
CAAGTACGCATGCAACTGCGTTGTTGGCTACATCGGCGAACGTTGCCAGTACCGT
 K   Y   A   C   N   C   V   V   G   Y   I   G   E   R   C   Q   Y   R

BamHI                       BamHI
GACCTGAAATGGTGGGAACTGCGTTAAGGATCCGTGACTAATTGGGGA
                        (BamHI site of pBM11)

Trans. Term.                         |
CCCTAGAGGTCCCCTTTTTTATTTTAAAACGATCC
```

EXAMPLE IX

Isolation of Recombinant Polypeptides

A. Growth Factors Produced in pBM-Based Vectors Using the PL Promoter and the ts CI Repressor

*E. coli* B (HB101) containing the pBM11/NDP/growth factor plasmids were grown in Luria Broth at 30° C. The density of the culture was measured at 550 nm and when the density reached an absorbance of 0.7 to 0.9, synthesis of the growth factor fusion protein was induced by increasing the temperature to 42° C. The culture was incubated at this temperature for 5–20 hrs, then the bacteria were isolated by centrifugation and frozen at −70° C. until use.

For isolation of the recombinant protein, the cells were thawed into buffer containing 0.05 M $NaH_2PO_4$ pH 7.2, 0.5 M NaCl, 0.01 M EDTA. One hundred fifty ml of buffer was used for a preparation from 50 g bacteria. The cells were disrupted by sonication on ice for 15 min using a ¼-inch probe, 50% pulse at 60 watts of power. Following disruption of the cells, the insoluble protein was collected by centrifugation at 12,000 rpm in a GSA rotor for 90 min. The pellet containing the insoluble protein was then resuspended in 50 ml of 6 M guanidine hydrochloride. The insoluble material was collected by centrifugation for 2 hrs at 25,000 rpm in a Beckman-type 30 ultracentrifuge rotor. The supernatant was collected and stored at −20° C. until further use.

Purification of the fusion protein was carried out on either a Sephacryl S300 or Fractogel HW-55 column equilibrated with 1 M guanidine hydrochloride. Fractions containing the fusion protein were identified as those fractions containing a polypeptide having a molecular weight consistent with the molecular weight of the polypeptide encoded by the synthetic gene as determined on a 15% polyacrylamide-urea gel.

To obtain an active form of the recombinant growth factor, the fusion protein was allowed to refold by incubating it in 50 mM Tris-HCl buffer, pH 8.7, containing 1 M guanidine hydrochloride, 1.25 mM reduced glutathione, and 0.25 mM oxidized glutathione at 4° C. for 3–10 days. The biological activity of the growth factor was monitored by a competitive receptor binding assay as described above (see Example I.C). When a maximum level of activity was obtained, the protein was dialyzed against distilled water and lyophilized to dryness.

If it was desired to remove the leader sequence, the protein was cleaved either by resuspending in 70% formic acid and incubating at 40° C. for 3 days or by incubating overnight at room temperature in a 100-fold molar excess of cyanogen bromide. The cleaved product was dialyzed against distilled water and lyophilized to dryness.

To further purify the recombinant growth factor, the growth factor was resuspended in 40% acetonitrile, 0.1% TFA and purified by HPLC using a BioRad TSK-250 column. Fractions containing the growth factor were pooled and further purified using reversed-phase HPLC, either Waters μBondapak C-18 or Rainin Dynamax C-8. The eluant was a linear gradient of 20–40% acetonitrile containing 0.1% TFA. Fractions containing receptor binding activity were pooled, lyophilized and stored at −20° C. until use.

1. TGF and Modified TGF a. N/TGF

Recombinant modified human TGF was produced from plasmid pBM11/N/TGF and contained 33 amino acids of the N-gene at the N-terminus and the sequence modification QEEK instead of the natural human sequence QEDK.

2. Modified and Truncated VGF a. PAD/nVGFa

Recombinant modified VGF was produced from plasmid pBM11/PAD/nVGFa containing the extreme N-terminal sequence of VGF and the modified sequences GTC and GYACRC instead of the natural VGF sequence GDC and GMYCRC. The nVGFA fragment was expressed as a fusion protein with a modified alkaline phosphatase signal sequence at the N-terminus and was truncated at the sequence YQR at the C-terminus.

b. NDP/VGFa

Recombinant modified VGF was produced from plasmid pBM11/NDP/VGFa beginning at the DIPAIR sequence and ending at the YKQR sequence in VGF. It has the modified sequences GTC and GYACRC instead of the natural VGF sequence GDC and GMYCRC. The VGFa fragment was expressed as a fusion protein with 32 amino acids of the N-gene at the N-terminus and the acid labile dipeptide aspartic acid-proline.

c. VGFa

The VGF fragment was prepared as described in 2.b above and, after cleavage from the fusion protein by acid treatment, was subsequently further purified by HPLC.

d. NDP/VGFA

Recombinant modified VGF was produced from plasmid pBM11/NDP/VGFA beginning at the DIPAIR sequence and ending at the YKQR sequence in VGF and having the modified sequences GTC and GYACVC instead of the natural VGF sequence GDC and GMYCRC. The VGFA fragment was expressed as a fusion protein with 32 amino acids of the N-gene at the N-terminus and the acid labile dipeptide aspartic acid-proline.

3. Chimeric TGF/VGF Hybrids a. N/TTV (TGF/TGF/VGF)

Recombinant modified TTV was produced from pBM11/N/TTV and contained the amino acid sequence of human TGF in the amino terminal two-thirds of the gene with the exception of the sequence QEEK which was altered from the natural human sequence QEDK. The carboxy terminus was derived from the amino acid sequence of VGF and terminated with the sequence YQR upstream of the natural sequence PNT. The TTV fragment was expressed as a fusion protein with 33 amino acids of the N-gene at the N-terminus.

b. NDP/TTV

Recombinant TTV was produced from plasmid pBM11/N/TTV and modified as described in (a) except that the TTV fragment was expressed as a fusion protein with 32 amino acids of the N-gene at the N-terminus and the acid labile dipeptide aspartic acid-proline.

c. NDP/VTV

Recombinant modified VTV was produced from plasmid pBM11/NDP/VTV and contained the amino acid sequence of human TGF in the middle domain with the amino acid sequence QEEK replacing the natural sequence QEDK. The N-terminal and C-terminal domains were derived from the truncated VGF sequence and begin with the sequence DIPAIR and end with the sequence YQR. The VTV fragment was expressed as a fusion protein with 32 amino acids of the N-gene at the N-terminus and the acid labile dipeptide aspartic acid-proline.

d. NDP/TVV

Recombinant modified VTV was produced from plasmid pBM11/NDP/TVV and contained the amino acid sequence of human TGF in the N-terminal domain of the gene. The middle and C-terminal domains were derived from the truncated VGF sequence and end with the sequence YQR. In addition, the synthetic gene has the modification GYACVC for GMYCRC. The TVV fragment was expressed as a fusion protein with 32 amino acids of the N-gene at the N-terminus and the acid labile dipeptide aspartic acid-proline.

B. Growth Factors Produced in Vectors Comprising the Tac or Lac Promoters

Bacterial hosts containing expression cassettes which comprise the tac or lac promoters were grown at 30 to 37° C. to an optical density of A600=0.2 to 0.8 in either LB broth or a chemcially defined medium such as M9 medium supplemented with thiamine and glucose. Am appropriate antibiotic was included in the growth medium to select for hosts containing the expression cassette. The bacterial cultures were induced with 100 to 1000 mM concentrations of IPTG and were allowed to grow at 30° C. for 16 to 24 hours. For the expression cassettes lacking a lacI gene the bacterial hosts carried an F-factor with the lacIq gene, such as JM109, XL1, JM103, etc. For expression cassettes which carry the lacI gene, examples of bacterial hosts are HB101, DH1, DH5, etc. In the case where the bacterial host has a functional lac operon (lac+), the expression cassette can be induced with 1% lactose. After the induction period, growth factors can be isolated from either the medium or the cell pellet.

1. PAK/EGF

Human EGF produced from the expression cassettes TacPak/EGF and pTCPt/EGF was isolated from the medium in an active form with the alkaline phosphatase signal sequence removed. Approximately 85% of the active EGF is found in the medium, with the remainder associated with the call pellet. These expression cassettes have yielded 4 mg/l of active EGF. The cells are removed from the medium by centrifugation and the medium is passed through an Amicon SY30, 30,000 $M_r$ cutoff spiral filter and then passed through a Q-Sepharose column and the highly purified human EGF was eluted in 20 mM $NaPO_4$ pH7 with a 0 to 0.5 M NaCl gradient. Alternatively, the growth factors can be isolated from the cell pellet by osmotic shock or sonication and purified by essentially the same procedure.

2. PAK/nVGFa

Recombinant nVGFa was produced from the expression cassette pTCPt/nVGFa. The nVGFa was isolated from the cell pellet by sonication and was shown to constitute approximately 40% of the total bacterial protein.

C. Platelet Factor 4

Recombinant Platelet Factor 4 was isolated essentially as described above for growth factors.

1. N/PF4

Recombinant Platelet Factor 4 was produced from pBM11/N/PF4 as a fusion with the 33 N-terminal amino acids of the N-protein.

2. NDP/PF4

Recombinant Platelet Factor 4 was produced from pBM11/NDP/PF4 as a fusion with the 33 N-terminal amino acids of the N-protein and an aspartic-acid-proline cleavage site. Treatment of the fusion protein with formic acid released the mature PF4.

D. Oncostatin M

1. NDP/Oncostatin M a. Purification of Recombinant Oncostatin M

Recombinant Onco M fusion proteins were purified from *E. coli* as follows: A cell pellet from a 500 ml culture of *E. coli* was suspended in 40 ml of PNE buffer (0.5 M NaCl, 10 mM EDTA, 50 mM sodium phosphate), and lysed by sonication. Aggregated proteins were collected from the cell lysate by centrifugation. Aggregated proteins were sequentially extracted for 16 hrs each with 120 ml of 8 M urea solutions buffered as follows: Solution 1) 20 mM Tris, pH 5; Solution 2) 20 mM Tris, pH 8; Solution 3) 50 mM Tris, pH 11. Most aggregated proteins were solubilized by Solutions 1 and 2, while recombinant Onco M remained insoluble until treatment with Solution 3.

b. Refolding of Recombinant Molecules

The Solution 3 extract was then dialyzed for 24 hrs against a refolding buffer (1 M guanidine HCl, 1.2 mM oxidized glutathione, 0.2 mM reduced glutathionine, 20 mM Tris HCl, pH 8.0–9.0). Lowering the pH to <pH 8.0 resulted in a 100-fold reduction in yield of biologically active Onco M. Following re-folding, proteins were dialyzed versus 1 N acetic acid before testing in the growth inhibitor assay (Example I.E).

2. PAD/Oncostatin M

The PAD/OncoM was prodduced from the expression cassette pBM11/PAD/OncoM. The medium was tested for active OncoM and was shown to contain from 20 to 500 μg/l.

EXAMPLE X

Biological Activity of Recombinant Growth Factors Prepared in Procaryotic Cells

A. EGF Receptor Binding

This assay determines the ability of a molecule to bind to the EGF receptor as measured by its ability to inhibit the binding of EGF to its receptor. All growth factors and chimeric growth factors, whether modified or truncated, isolated to date were active in the EGF receptor binding inhibition assay. A summary of these results is shown below:

TABLE I

EGF Receptor Binding of Recombinant Growth Factors

| Peptide | Expression Cassette | Purity | Binds to EGF Receptor |
|---|---|---|---|
| N/TGF - modified truncated fusion | pBM11/N/TGF | 95% | Yes |
| PAD/nVGFa - modified truncated fusion | pBM11/PAD/nVGFa | >95% | Yes |
| NDP/VGFa - modified truncated fusion | pBM11/NDP/VGFa | >95% | Yes |
| NDP/VGFA - modified truncated fusion | pBM11/NDP/VGFA | >95% | Yes |
| N/TTV - modified truncated chimeric fusion | pBM11/N/TTV | >95% | Yes |
| NDP/TTV - modified truncated chimeric fusion | pBM11/NDP/TTV | >95% | Yes |
| NDP/VTV - modified truncated chimeric fusion | pBM11/NDP/VTV | >95% | Yes |
| NDP/TVV - modified truncated chimeric fusion | pBM11/NDP/TVV | >95% | Yes |
| PAK/EGF | pBM11/PAK/EGF | 95% | Yes |
| EGF | pBM11/PAK/EGF | 95% | Yes |
| PAD/EGF | pBM11/PAD/EGF | 95% | Yes |
| EGF | pBM11/PAD/EGF | 95% | Yes |
| PAK/EGF | TacPak/EGF | 95% | Yes |
| EGF | Tacpak/EGF | 95% | Yes |
| PAK/EGF | pTCPt/EGF | 95% | Yes |
| EGF | pTCPt/EGF | >95% | Yes |

A comparison of the binding inhibition curves for natural mouse EGF and the bacterially expressed recombinant chimeric growth factor N/TTV (a polypeptide fusion of the 32 N-terminal amino acids of the lambda N-gene and the modified and truncated TGF/VGF hybrid) suggested that there were no differences in the binding activity.

B. Mitogenic Activity

The activity of several of the purified growth factors was tested and the activity determined in all cases was comparable to the effect caused by EGF. The compounds tested are as indicated below:

TABLE II

| Mitogenic Activity of Growth Factors | |
|---|---|
| Peptide | Mitogenic Activity* |
| TTV - modified truncated chimeric | Yes |
| N/TTV - modified truncated chimeric fusion | Yes |

*As measured by $^3$H-thymidine or $^{125}$I-IdU incorporation.

C. Wound Healing

1. Mid-dermal Injuries

The effect of natural or synthetic TGF, EGF and VGF, as well as recombinant growth factors on mid-dermal injuries was assessed as described in Example VE1. The percent of the original burn area which had healed was measured by computer-assisted telemetry, and the percent wound re-epithelialization was determined. Untreated wounds were approximately 15% reepithelialized. Treatment with Silvadene alone or Silvadene with EGF resulted in approximately 50% reepithelialization, while treatment with synthetic TGF or natural VGF resulted in approximately 90% re-epithelialization. The optimal concentration to promote re-epithelialization of EGF was 1–10 μg/ml, while synthetic TGF and natural VGF produced a maximal response at 0.1 μg/ml.

Experiments similar to those described above were done to test the effect in wound healing of either TGF, a modified, truncated form of VGF (VGFa), or a modified, truncated chimeric fusion of TGF and VGF (TTV), all of which were produced by recombinant technology in bacteria. These recombinant growth factors and hybrid growth factors accelerated wound healing to the same extent as either synthetic TGF or natural VGF, with an optimal concentration at 0.1 μg/ml.

2. Mid-dermal Donor Graft Injuries

Modified truncated VGFa was assayed for its ability to accelerate wound healing in a donor graft model. The treatment regimen was as described above (see Example I) using 1 ml VGFa, 5 μg/ml, in 20 g Silvadene. Photographs were taken on a daily basis. A summary of the results is provided below:

TABLE III

Effect of Recombinant VGFa on Wound Healing

| | Wound Condition | | | |
|---|---|---|---|---|
| Treatment* | POD** 7 | POD 8 | POD 9 | POD 10 |
| Saline | very open | open with some healing | mostly healed | healed |
| VGFa - modified, truncated | open; apparent epitheli-alization | mostly healed | healed | healed |

*Silvadene is the vehicle
**POD = Post Operative Day

The modified truncated VGFa accelerated healing of the wound as compared to the carrier control. Photographs (not provided) at POD 8 showed substantial differences between saline and VGFa. The term of this patent shall not extend beyond the expiration date of Pat. No.

EXAMPLE XI

Biological Activity of Recombinant Platelet Factor 4 Prepared in Prokaryotic Cells The yield of recombinant Factor 4 prepared using different expression cassettes varied from about 2% to about 20% of total cell protein. These results are summarized below:

TABLE IV

| Expression of PF4 in Different Bacterial Expression Systems | |
|---|---|
| | Percent of Total Protein |
| pBM11/Ngene/PF4 | 20% |
| pBM11/Ngene/DP/PF4 | 20% |
| pBM11/PAD/PF4 | 15% |
| pBM11/PF4 | 2% |

A. Inhibition of DNA Synthesis

The highest activity seen was with the fusion protein from the plasmid pBM11/Ngene/PF4. Fifty percent of maximum inhibition of A549 cells was obtained with 0.67 μg/well.

B. Inhibition of Growth of Tumors in Nude Mice

Male nude mice were injected with platelet factor 4 or phosphate buffered saline at 2- to 3-day intervals, as described in Example 1C. As shown below, factor 4 significantly inhibited tumor growth.

TABLE V

Effect of Recombinant N-Gene Platelet Factor 4 Fusion Protein on Growth of Tumors in Nude Mice

| | Tumor size (mm$^3$) | |
|---|---|---|
| Days Post Treatment | Control | Platelet Factor 4 |
| 0 | 17 | 25 |
| 6 | 205 | 25 |
| 9 | 275 | 25 |
| 14 | 420 | 40 |
| 17 | 545 | 50 |
| 20 | 635 | 85 |

EXAMPLE XII

Biological Activity of Recombinant Oncostatin Prepared in Prokaryotic Cells

A. Physicochemical Characterization of Recombinant Oncostatin M

1. SDS-PAGE

Cultures (50 ml) were grown and induced as described. Cultures were pelleted and the cell pellets were solubilized in 6 M guanidine HC1. Insoluble proteins were not removed at this point. Samples for SDS-PAGE analysis were dialyzed directly against 1 N acetic acid without refolding.

Aliquots consisting of approximately 6 μg of total bacterial protein were analyzed by SDS-PAGE on 10–20% gradient gels (5% stacking gel). Gels were stained with Coomassie Brilliant Blue, destained and dried. The apparent molecular weight $M_r$ of the NDP-Onco M fusion protein was estimated to be 32,000 by comparison of its mobility with that of standard proteins.

B. Growth Inhibitory Activity of Recombinant Oncostatin M (N-Gene Fusion Protein)

Cellular proliferation in the presence of recombinant or native Oncostatin M was compared with proliferation in untreated samples, and expressed as a percentage of maximal (untreated) growth. Samples were assayed in duplicate or triplicate, and generally varied by less than 20% from each other. One growth inhibition assay unit of Oncostatin M is defined as the amount of protein required to cause a 50% inhibition of the growth of A375 cells seeded at 3 to 4×10$^3$ during a 72-hr assay. Where indicated, concentrations required for half-maximal growth inhibition were determined by extrapolation from proliferation data after transformation as follows:

$$\%\ \text{Maximal Inhibition} = 100 \times \frac{1 - (A_{590}\mathit{treated} - A_{590}\mathit{Maximal})}{A_{590}\mathit{untreated} - A_{590}\mathit{maximal}}$$

In some cases, a modified proliferation assay was used, in whihc the target cell number and serum concentration were reduced. Cells were seeded at 500 cells/well in DMEM containing 5% FBS, treated with Oncostatin M in the same medium, and incubated at 37° C. until untreated cells reached confluence (generally between 6 and 10 days, depending on the cell line). Monolayers were then stained and processed as described below:

TABLE VI

Growth Inhibitory Activity of Recombinant Oncostatin M

| Recombinant[1] Oncostatin M | | Native Oncostatin M | |
|---|---|---|---|
| pM | Percent Maximal Growth | pM | Percent Maximal Growth |
| 240 | 12.2 | 160 | 15.1 |
| 48 | 19.5 | 32 | 22.2 |
| 9.6 | 30.4 | 6.4 | 41.5 |
| 1.9 | 70.0 | 1.3 | 67.3 |
| 0.38 | 77.8 | 0.26 | 82.3 |
| 0.08 | 81.5 | 0.05 | 76.0 |
| | 86.4 | | 72.4 |
| | 85.9 | | 77.5 |
| 0 | 100.0 | 0 | 100.0 |

[1]Prepared using pBM11/NDP/OncoM expression cassette.

C. Receptor Binding Activity of Recombinant Oncostatin M (N-Gene Fusion Protein)

$A_{549}$ human lung carcinoma cells were incubated with $^{125}$I-Oncostatin M in the presence of increasing amounts of unlabeled Oncostatin M. A fraction (~3) of added $^{125}$I-Oncostatin M bound to these cells in the absence of unlabeled Oncostatin M. When binding was measured in the presence of unlabeled native or recombinant Oncostatin M, a concentration-dependent inhibition of binding of $^{125}$I-Oncostatin M was observed (half-maximal effect at ~300 pM). Total binding of $^{125}$I-Oncostatin M was inhibited by approximately 90% at the highest concentration of unlabeled Oncostatin M tested. Native and recombinant Oncostatin M did not differ significantly from each other in their abilities to inhibit binding of $^{125}$I-Oncostatin M. The results are as shown below:

TABLE VII

Receptor Binding Activity of Recombinant Oncostatin M

| Recombinant[1] Oncostatin M | | Native Oncostatin M | |
|---|---|---|---|
| pM | Percent Maximal Growth | pM | Percent Maximal Growth |
| 16,000 | 14 | 27,000 | 12 |
| 3,200 | 27 | 5,400 | 20 |
| 640 | 48 | 1,080 | 40 |
| 128 | 72 | 216 | 67 |
| 26 | 80 | 43.2 | 81 |
| 5.1 | 92 | 8.6 | 88 |
| 1 | 90 | 1.7 | 89 |
| 0 | 100 | 0 | 100 |

[1]Prepared using pBM11/NDP/OncoM expression cassette.

The compositions of the subject invention comprise expression casettes for the efficient expression of polypeptides in prokaryotic cells. The expression cassettes find use in production of large amounts of polypeptides by providing for increased stability of the expression products as well as for obtaining mature folded polypeptides secreted into the growth medium of the host cell.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An expression cassette for the secretion of a disulfide bond-containing polypeptide in a biologically active, mature form from an *E. coli* host cell into the culture medium, said cassette having DNA segments operably linked with each other as follows:

P--S.D.--met--L--G--T wherein

P consists essentially of a promoter having a −35 consensus regulatory sequence from the trp promoter and a −10 consensus regulatory sequence from the lac promoter;

S.D. consists essentially of a Cro gene Shine-Dalgarno sequence;

met consists essentially of a codon for an initiating methionine;

L consists essentially of a first DNA sequence encoding an *E. coli* alkaline phosphatase signal sequence, wherein the codons for the amino acids of said signal sequence are modified using codon degeneracy so that the nucleotides encoding said signal sequence approximate those of the native nucleotide sequence associated with said S.D.;

G consists essentially of a second DNA sequence encoding the mature polypeptide; and T consists essentially of a transcriptional termination region having a guanine:cytosine-rich region capable of forming a stem-loop structure in the corresponding RNA transcript, followed by a string of thymines; said S.D. being operably linked downstream from said P and upstream from said met, said L being operably linked downstream from said met and upstream from said G, and said T being operably linked downstream from said G.

* * * * *